US009248170B2

(12) United States Patent
Kim et al.

(10) Patent No.: US 9,248,170 B2
(45) Date of Patent: Feb. 2, 2016

(54) IMMUNOGENIC COMPOSITIONS AND METHODS FOR TREATING NEOPLASIA

(71) Applicants: Young Jun Kim, Yongin (KR); Drew M. Pardoll, Brookeville, MD (US); Charles George Drake, Baltimore, MD (US); Meghan Davis, Baltimore, MD (US); Juan Fu, Baltimore, MD (US)

(72) Inventors: Young Jun Kim, Yongin (KR); Drew M. Pardoll, Brookeville, MD (US); Charles George Drake, Baltimore, MD (US); Meghan Davis, Baltimore, MD (US); Juan Fu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/663,045

(22) Filed: Oct. 29, 2012

(65) Prior Publication Data

US 2013/0177625 A1 Jul. 11, 2013

Related U.S. Application Data

(63) Continuation of application No. PCT/US2011/034139, filed on Apr. 27, 2011, and a continuation-in-part of application No. PCT/US2010/052889, filed on Oct. 15, 2010.

(60) Provisional application No. 61/328,471, filed on Apr. 27, 2010.

(51) Int. Cl.

| | | |
|---|---|---|
| A61K 38/18 | (2006.01) | |
| C12N 15/27 | (2006.01) | |
| A61K 35/12 | (2015.01) | |
| A61K 39/00 | (2006.01) | |
| A61K 45/06 | (2006.01) | |
| A61K 38/19 | (2006.01) | |
| A61K 31/7024 | (2006.01) | |
| A61K 31/739 | (2006.01) | |
| A61K 35/36 | (2015.01) | |
| A61K 35/38 | (2015.01) | |
| A61K 35/39 | (2015.01) | |
| A61K 35/55 | (2015.01) | |
| A61K 38/12 | (2006.01) | |

(52) U.S. Cl.
CPC ......... *A61K 39/0005* (2013.01); *A61K 31/7024* (2013.01); *A61K 31/739* (2013.01); *A61K 35/12* (2013.01); *A61K 35/36* (2013.01); *A61K 35/38* (2013.01); *A61K 35/39* (2013.01); *A61K 35/55* (2013.01); *A61K 38/193* (2013.01); *A61K 39/0011* (2013.01); *A61K 45/06* (2013.01); *A61K 2039/5152* (2013.01); *A61K 2039/5156* (2013.01); *A61K 2039/55511* (2013.01); *A61K 2039/55522* (2013.01); *A61K 2039/55572* (2013.01)

(58) Field of Classification Search
None
See application file for complete search history.

(56) References Cited

U.S. PATENT DOCUMENTS

| | | | |
|---|---|---|---|
| 5,637,483 A | 6/1997 | Dranoff et al. | |
| 2004/0197312 A1* | 10/2004 | Moskalenko et al. | 424/93.21 |
| 2008/0075705 A1 | 3/2008 | Tran | |
| 2008/0145375 A1 | 6/2008 | Bembridge et al. | |
| 2009/0081157 A1 | 3/2009 | Kornbluth et al. | |

FOREIGN PATENT DOCUMENTS

| | | |
|---|---|---|
| JP | 2006-525995 A | 11/2006 |
| JP | 2007-505827 A | 3/2007 |
| JP | 2007-530430 A | 11/2007 |
| WO | WO-96/40267 A1 | 12/1996 |
| WO | WO-2005-013891 A2 | 2/2005 |
| WO | WO-2005/025614 A2 | 3/2005 |
| WO | WO-2006/116423 A2 | 11/2006 |
| WO | WO-2008/153541 A1 | 12/2008 |
| WO | WO-2010024897 A2 | 3/2010 |
| WO | WO-2011/053223 A1 | 5/2011 |

OTHER PUBLICATIONS

Van Den Eertwegh et al, (Journal of Clinical Oncology, 2006 ASCO Annual Meeting Proceeding, Vol .24, No. 18S (Jun. 20, Supplement, 2006: 2530.*
Eager et al, Molecular Therapy vol. 12, No. 1, p. 18-27.*
Davis et al, Clinical Cancer Research, 2011; vol. 17, No. 12, pp. 3984-3992.*
Goldstein et al, 51th Ash Annual Meeting and Exposition, Online programs and Abstracts, abstract #929, Dec. 3, 2009.*
M. Jinushi, et al, "MFG-E8-Mediated Uptake of Apoptotic Cells by APCS Links the Pro- and Antiinflammatory Activities of GM-CSK" J Clin Invest., 2007, vol. 117, No. 7, pp. 1902-1913.
S. Fukuzono, et al., "Granulocyte Colony-Stimulating Factor Negatively Regulates Toll-Like Receptor Agonist-Induced Cytokine Production in Human Neutrophils", Arch Biochem Biophys. Epub Jan. 12, 2010, vol. 495,No. 2, pp. 144-151.
WK Decker, "Bioimmunoadjuvants for the Treatment of Neoplastic and Infectious Disease: Coley's Legacy Revisited", Cytokine Growth Factor Rev., Epub Aug. 4, 2009, vol. 20, No. 4, pp. 271-281.
International Preliminary Report on Patentability, for International Patent Application No. PCT/US2011/034139, mailed on Nov. 8, 2012.
Brosbol-Ravnborg A. et al. "Toll-Like Receptor Induced Granulocyte-Macroph Age Colony-Stimulating Factor Secretion is Impaired in Crohn's Disease by Nu Cleotide Oligomerization Domain 2-Dependent and Independent Pathways" Clin. Exp. IMMUNOL, vol. 155, No. 3, 2009, pp. 487-495.

(Continued)

*Primary Examiner* — Bridget E Bunner
*Assistant Examiner* — Fozia Hamud
(74) *Attorney, Agent, or Firm* — Mintz Levin Cohn Ferris Glovsky and Popeo, P.C.; Peter F. Corless, Esq.; Daniel W. Clarke

(57) ABSTRACT

The invention provides provides immunogenic compositions comprising neoplastic cells expressing a cytokine (GM-CSF) formulated with at least one TLR agonist and methods of using the composition to induce or enhance an immune response.

20 Claims, 13 Drawing Sheets

(56) References Cited

OTHER PUBLICATIONS

Kornbluth R.S. et al. "Immunostimulatory Combinations: Designing the Next Generation of Vaccine Adjuvants" Journal of Leukocyte Biology, vol. 80, pp. 1084-1102; 2006.

Schaefter T.M. et al. "Toll-Like Receptor (TLR) Expression and TLR-Mediated Cytokine/Chemokine Production by Human Uterine Epithlial Cells"; IMMUNOLOGY, vol. 112, No. 3, 2004, pp. 428-436.

K. M. Kege et al., "GM-CSF Gene-Modified Cancer Cell Immunotherapies: Of Mice and Men;" Int Reviews of Immunology, vol. 25, 2006, pp. 321-352.

Kandalaft et al. "The Emergence of Immunomodulation: Combinatorial Immunochemotherapy Opportunities for the Next Decade." *Gynecol. Oncol.* 116.2(2010):222-233.

* cited by examiner

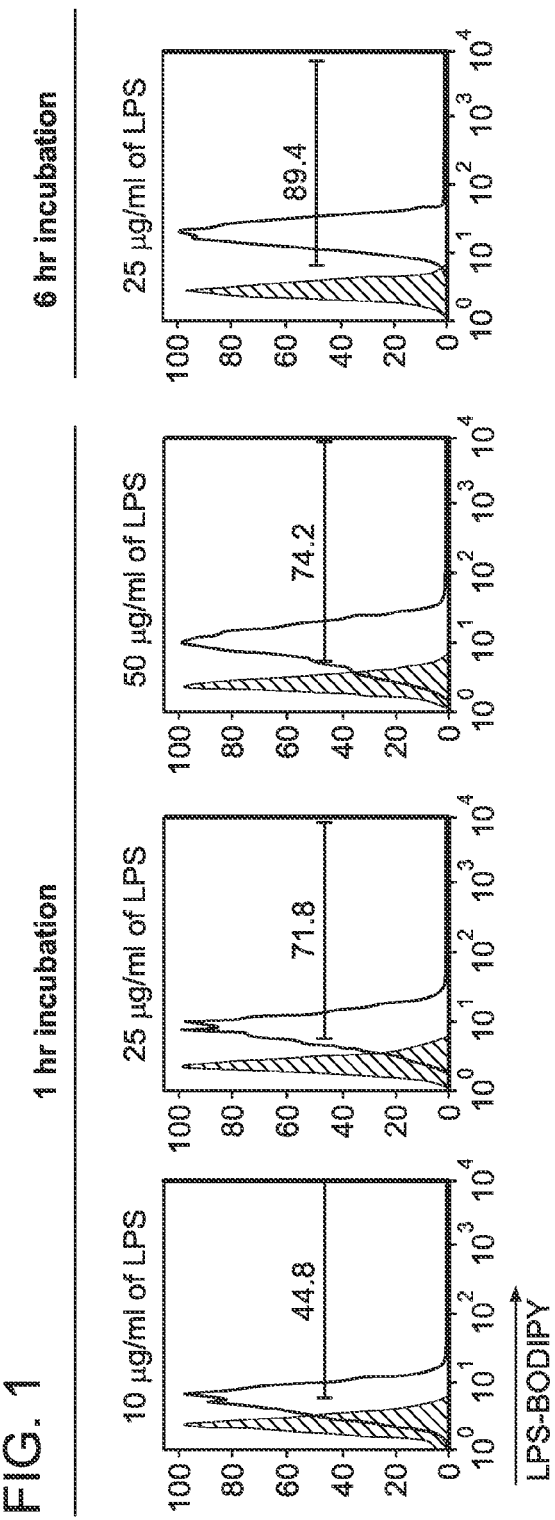
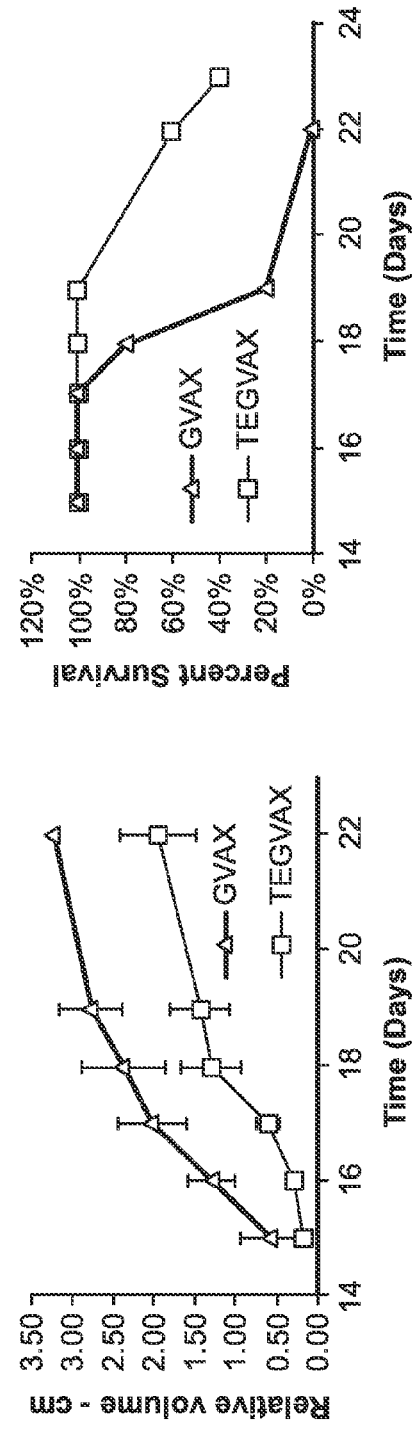
FIG. 1
FIG. 2A

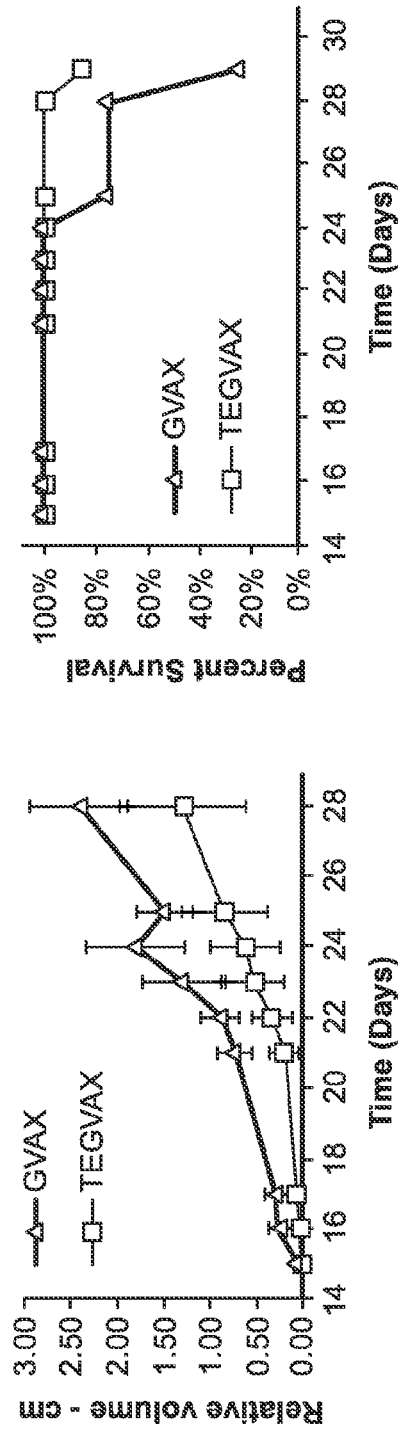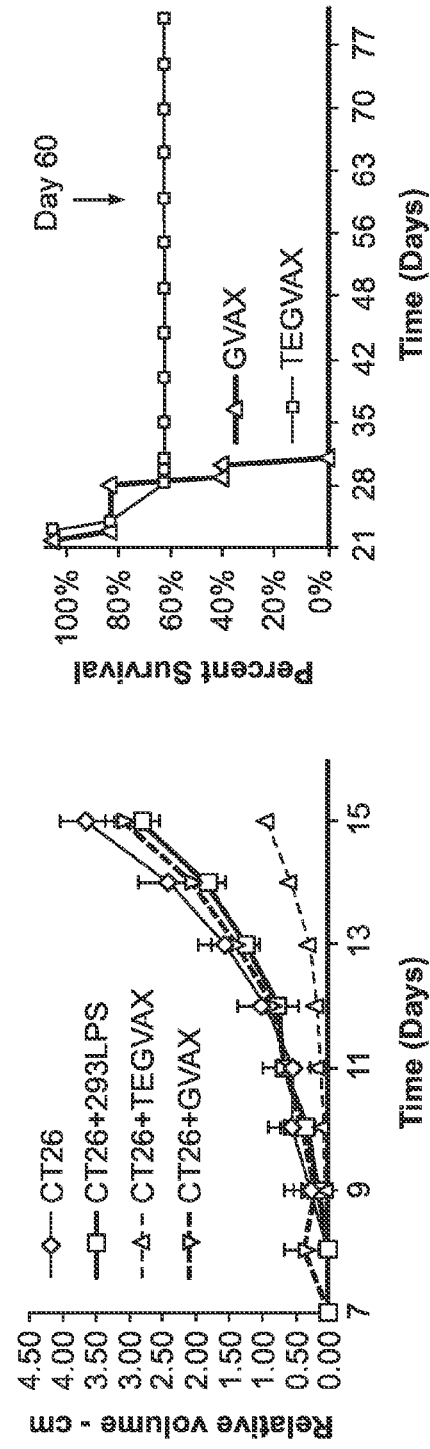

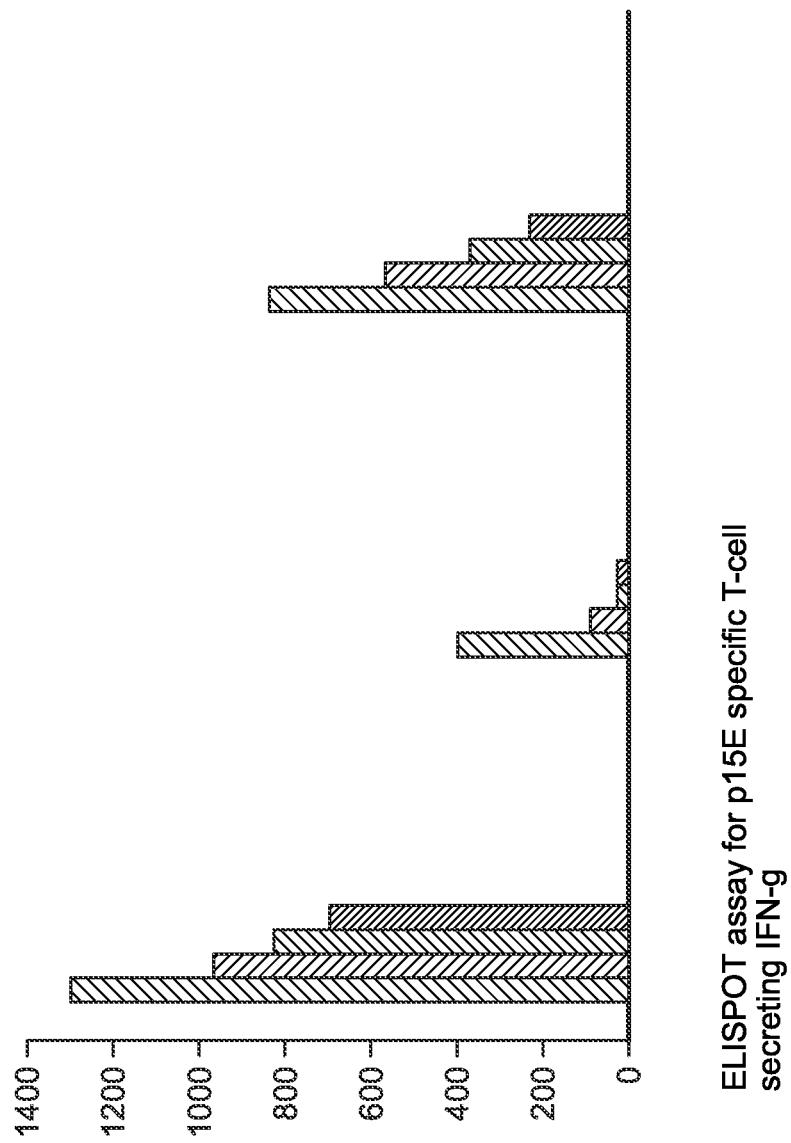

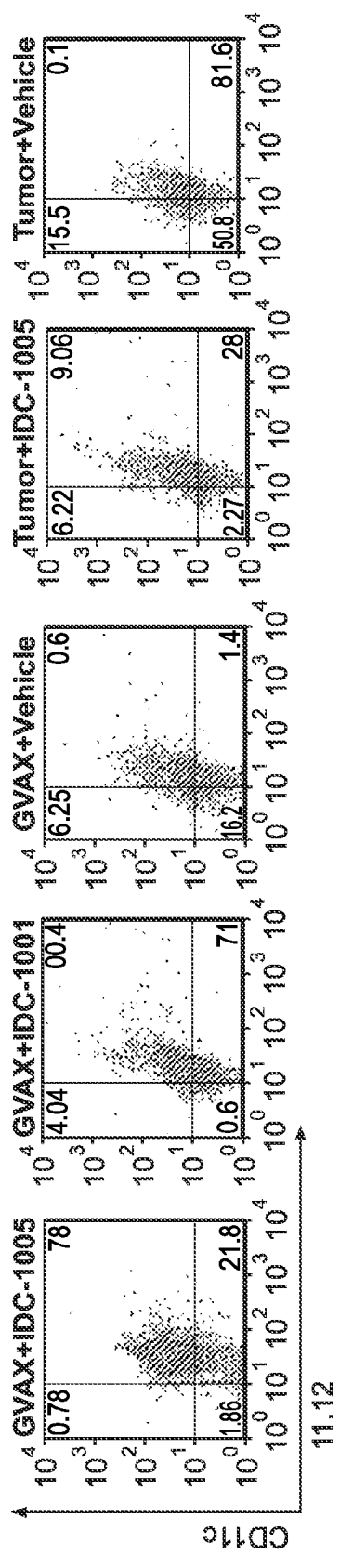
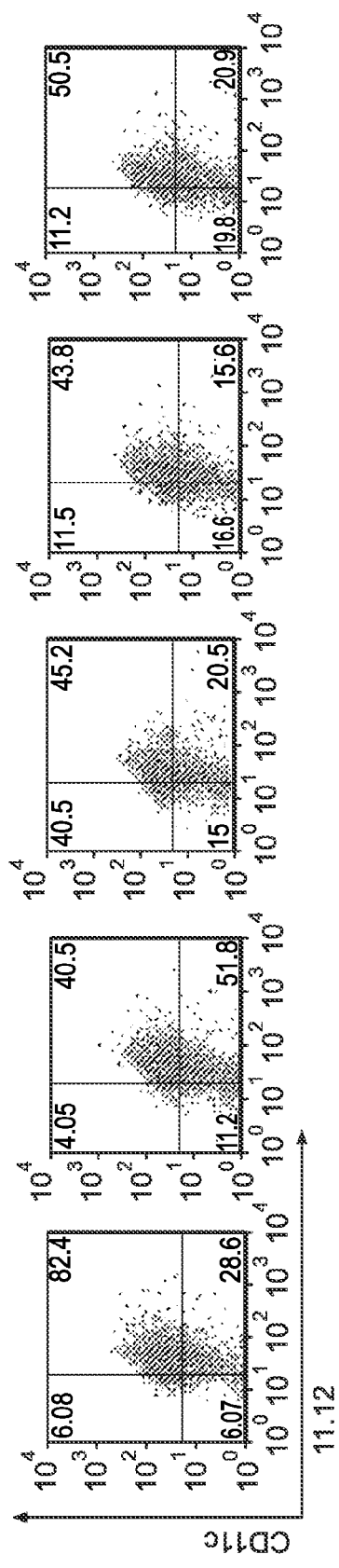
FIG. 13A
FIG. 13B

SEQUENCE LISTING

```
<160> NUMBER OF SEQ ID NOS: 4

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Val Val Pro Pro
1               5

<210> SEQ ID NO 2
<211> LENGTH: 144
<212> TYPE: PRT
<213> ORGANISM: Homo sapiens

<400> SEQUENCE: 2

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
        130                 135                 140

<210> SEQ ID NO 3
<211> LENGTH: 5992
<212> TYPE: DNA
<213> ORGANISM: Homo sapiens

<400> SEQUENCE: 3
```

-continued

```
gcagtctgtt tcctaccaga ctgggagcct caagggccaa atgtgagggc cagtgggagg      60
gtcccgttta cctccccaga acaggtcctg gtgtggattg aaagacttg ttgactgact      120
gtctgagcta tgacaactca tttctaggag gaaagtgacc ttctctccca gatgggtcat     180
acaggctctc tgcctccctg gccatcagct gaaccactat ctatggctcc cttccctgcc     240
ctccagcctc cagggtgcta tccaacacat gtgatatcta catgtagtat ccatgtcctc     300
atctctcccc cgagagctcc ctggaaagag ctgagccaag gccttgcaaa aaggtggag      360
aaagggccag ggcctggaca tttcatgttc ccaccccagc ctggccacta ggagtgttct     420
acgcaggctc agatggatgg ggctggcctc acagtgggt ctggaggact aaggtttggt      480
ttctctatgc aaggtcagaa aaactcccac agtacaggga aactggccag ggctgcagac     540
tcagaccaca gtgctaaagc catgaactcc acctgctctc tgaaggctcg ccaacctgag     600
tccagcagaa tgttctcgct tgtgtccaac cccactggtt taggctgaat cagcctctag     660
ggcccagagg cactgcacct ggagtaggga gcttctccag tatcagagtc accttcagag     720
gcctggagcc tttcataaag caggtaagag gactcaatag atgcatctgc atggaaaaca     780
tcctcccctc taccaggcac ctgtatgtac aaccaatcac agcagcacac atacacccag     840
aaatgggcac gtgtgggccc acccccttt agctatgaaa cccaggcatg gggcagcttg      900
agccagatac cttgtgcaaa cacaaactcg tgctgtcttc tctgaactcc attgtgaaaa     960
tcaaacactt gtcagcccct caagagcctt tagatttcct acttccacac ttccacgaaa    1020
aggcctctgg agttgggga tgctgggtt atgtaggaaa ttaagcctgg agggccttgc      1080
tggggaagcc attgtccctg tacctgagat ggatgcagcc acagccctgg agccagcctg    1140
aagctcctgg tgtcttctgg gggctacata taggagtgta gtccgaacct cagaggggca    1200
aacctgctct gcagagggaa tcaaggttca cataaccaga gaggggagtc actcaggaag    1260
gtggctccag agccaagagt cagactctgg gtcccgactt gacccagcca cacccccttct   1320
gaagcttgct gagagtggct gcagtctcgc tgctggatgt gcacatggtg gtcattccct    1380
ctgctcacag gggcaggggt ccccccttac tggactgagg ttgcccccctg ctccaggtcc   1440
tgggtgggag cccatgtgaa ctgtcagtgg ggcaggtctg tgagagctcc cctcacactc    1500
aagtctctca cagtggccag agaagaggaa ggctggagtc agaatgaggc accagggcgg    1560
gcatagcctg cccaaaggcc cctgggatta caggcaggat ggggagccct atctaagtgt    1620
ctcccacgcc ccacccccagc cattccaggc caggaagtcc aaactgtgcc cctcagaggg    1680
agggggcagc ctcaggccca ttcagactgc ccagggaggg ctggagagcc ctcaggaagg    1740
cgggtgggtg ggctgtcggt tcttggaaag gttcattaat gaaaaccccc aagcctgacc    1800
acctagggaa aaggctcacc gttcccatgt gtggctgata agggccagga gattccacag    1860
ttcaggtagt tcccccgcct ccctggcatt ttgtggtcac cattaatcat ttcctctgtg    1920
tatttaagag ctcttttgcc agtgagccca gtacacagag agaaaggcta agttctctg     1980
gaggatgtgg ctgcagagcc tgctgctctt gggcactgtg gcctgcagca tctctgcacc   2040
cgcccgctcg cccagcccca gcacgcagcc ctgggagcat gtgaatgcca tccaggaggc   2100
ccggcgtctc ctgaacctga gtagagacac tgctgctgag atggtaagtg agagaatgtg   2160
ggcctgtgcc taggccaccc agctggcccc tgactggcca cgcctgtcag cttgataaca   2220
tgacattttc cttttctaca gaatgaaaca gtagaagtca tctcagaaat gtttgacctc   2280
caggtaagat gcttctctct gacatagctt tccagaagcc cctgccctgg ggtggaggtg   2340
gggactccat tttagatggc accacacagg gttgtccact ttctctccag tcagctggct   2400
```

```
gcaggaggag ggggtagcaa ctgggtgctc aagaggctgc tggccgtgcc cctatggcag    2460
tcacatgagc tcctttatca gctgagcggc catgggcaga cctagcattc aatgccagg     2520 agtcaccagg ggacaggtgg taaagtgggg gtcacttcat gagacaggag ctgtgggttt    2580
ggggcgctca ctgtgccccg agaccaagtc ctgttgagac agtgctgact acagagaggc    2640
acagaggggt ttcaggaaca acccttgccc acccagcagg tccaggtgag gccccacccc    2700
cctctccctg aatgatgggg tgagagtcac ctccttccct aaggctgggc tcctctccag    2760
gtgccgctga gggtggcctg gcggggcag tgagaagggc aggttcgtgc ctgccatgga     2820
cagggcaggg tctatgactg gacccagcct gtgcccctcc caagccctac tcctgggggc    2880
tgggggcagc agcaaaaagg agtggtggag agttcttgta ccactgtggg cacttggcca    2940
ctgctcaccg acgaacgaca ttttccacag gagccgacct gcctacagac ccgcctggag    3000
ctgtacaagc agggcctgcg gggcagcctc accaagctca agggcccctt gaccatgatg    3060
gccagccact acaagcagca ctgccctcca accccggtga gtgcctacgg cagggcctcc    3120
agcaggaatg tcttaatcta gggggtgggg tcgacatggg gagagatcta tggctgtggc    3180
tgttcaggac cccaggggt ttctgtgcca acagttatgt aatgattagc cctccagaga     3240
ggaggcagac agcccatttc atcccaagga gtcagagcca cagagcgctg aagcccacag    3300
tgctccccag caggagctgc tcctatcctg gtcattattg tcattatggt taatgaggtc    3360
agaggtgagg gcaaacccaa ggaaacttgg ggcctgccca aggcccagag gaagtgccca    3420
ggcccaagtg ccaccttctg gcaggacttt cctctggccc cacatggggt gcttgaattg    3480
cagaggatca aggaagggag gctacttgga atggacaagg acctcaggca ctccttcctg    3540
cgggaaggga gcaaagtttg tggccttgac tccactcctt ctgggtgccc agagacgacc    3600
tcagcccagc tgccctgctc tgccctggga ccaaaaaggc aggcgtttga ctgcccagaa    3660
ggccaacctc aggctggcac ttaagtcagg cccttgactc tggctgccac tggcagagct    3720
atgcactcct tggggaacac gtgggtggca gcagcgtcac ctgacccagg tcagtgggtg    3780
tgtcctggag tgggcctcct ggcctctgag ttctaagagg cagtagagaa acatgctggt    3840
gcttccttcc cccacgttac ccacttgcct ggactcaagt gttttttatt tttctttttt    3900
taaaggaaac ttcctgtgca acccagatta tcacctttga agtttcaaa gagaacctga    3960 aggactttct gcttgtcatc ccctttgact gctgggagcc agtccaggag tgagaccggc    4020
cagatgaggc tggccaagcc ggggagctgc tctctcatga acaagagct agaaactcag    4080 gatggtcatc ttggagggac caaggggtgg gccacagcca tggtgggagt ggcctggacc    4140
tgccctgggc cacactgacc ctgatacagg catggcagaa gaatgggaat attttatact    4200
gacagaaatc agtaatattt atatatttat atttttaaaa tatttattta tttatttatt    4260
taagttcata ttccatattt attcaagatg ttttaccgta ataattatta ttaaaaatat    4320
gcttctactt gtccagtgtt ctagtttgtt tttaaccatg agcaaatgcc agtggtgcct    4380
gccttcccat gaggcagggg agggaggaaa cggggaggtg gagagggggc ggggcctcc    4440 caggcgttgg gcactatcca agggccaaca ctgtcagagc agaggggagg tgagagccgg    4500
gcataggtgc ggaattctgc acacctggac gggcttcccg ggatgctcca gggctcccac    4560
cccagagaat ggctctcaag ttcacctgga agtccaagtg accagcccag ggaactctta    4620
tcccagagaa gggcaccacc cttcctgggg aggcctgggg gttggctggt cactggctga    4680
acaggcccac tctggcatca ggcaaaacac ctgccctgta gaggccttgg ccctgtgcc    4740
```

```
ccacgccctg cccctcacac tctgagattt aaccattccg aaagtaaaca gcaaaataga    4800
ctaactgttc aggggaaaag aaaccaaacc acagggtca cagtgcagcg tatttaccaa     4860
acttgcccca aaatgggtga tcttaatctc tgagagtcag aatgtaaggt cataatttgt   4920
tggtacatgg ctgtagtgcc gcatgttcct gaattggttt ttattttac atgaaattt     4980 gaatctaatc aggcactttc ccctaaaact catggcctgc aggctaaaaa caaagtaggc   5040
ctcctcctcc tccttacttt gacagctggg ctcaaggcct tgttcctgaa cctgttccct   5100
catctccctc caggactatg aggaagtgga tgtgccccaa gtcttaggcg ggcagcaggg   5160
ccagcttctc cttgacaggt gggcctaagg aagctggctt gtggcagctt tagcccctgc   5220
ctggcactgt ctgcagtcat gcgcccacca cccctcttgc ttcctctact tcagtcagca   5280
cctgcagaca gcgccaggcc tggcagaga cccactccat gctcatgcag aaagaccgtg    5340
acttcaggtg tgattacaaa taagaagtca gggtgaacgc tcaggatgaa gcctgagtgt   5400
cagcacaggc aagaatccat gaagtgtgct gtggttgttg aaaatgcatg aaaatcacat   5460
cttgcccagc gataaggtcc tctctgtctt ccgcgtaagc cagtgatgac tgataagagg   5520
tttagcattt ccttagcctc acatatatag gtacccctct ccacagaaat gctgccaagc   5580
ccagggctcg gaccagcttg gagtcacctt caagtaatac catgcacctg tacgtgctcc   5640
tggctcatgt gctctggggg tcagaaagcc attcttccca atgaaagtag ccacgatatc   5700
tccccacgaa aagtacacag cagtctgtgc tgacattcag aaagaactct cggctgacaa   5760
taacacacac aagataagtc tgggtctcca tcaaacgtta ttttgctctt agtgcccctt   5820
tgtgctcctg accaatttct ctggcttccg gggtcccttc aataggcccc agaaaaccag   5880
tgaggtaaga aacagctgcc ccgggacctt tcataccaca tttgaacagg gagagagaga   5940
tctcaccagt cagtgcccag ggaagagata acaacaaggg atagtggagt ga           5992
```

<210> SEQ ID NO 4
<211> LENGTH: 839
<212> TYPE: PRT
<213> ORGANISM: Homo sapiens

<400> SEQUENCE: 4

```
Met Met Ser Ala Ser Arg Leu Ala Gly Thr Leu Ile Pro Ala Met Ala
1               5                  10                  15

Phe Leu Ser Cys Val Arg Pro Glu Ser Trp Glu Pro Cys Val Glu Val
                20                  25                  30

Val Pro Asn Ile Thr Tyr Gln Cys Met Glu Leu Asn Phe Tyr Lys Ile
            35                  40                  45

Pro Asp Asn Leu Pro Phe Ser Thr Lys Asn Leu Asp Leu Ser Phe Asn
        50                  55                  60

Pro Leu Arg His Leu Gly Ser Tyr Ser Phe Phe Ser Phe Pro Glu Leu
65                  70                  75                  80

Gln Val Leu Asp Leu Ser Arg Cys Glu Ile Gln Thr Ile Glu Asp Gly
                85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
        115                 120                 125

Gln Lys Leu Val Ala Val Glu Thr Asn Leu Ala Ser Leu Glu Asn Phe
    130                 135                 140

Pro Ile Gly His Leu Lys Thr Leu Lys Glu Leu Asn Val Ala His Asn
145                 150                 155                 160
```

```
Leu Ile Gln Ser Phe Lys Leu Pro Glu Tyr Phe Ser Asn Leu Thr Asn
                165                 170                 175

Leu Glu His Leu Asp Leu Ser Ser Asn Lys Ile Gln Ser Ile Tyr Cys
            180                 185                 190

Thr Asp Leu Arg Val Leu His Gln Met Pro Leu Leu Asn Leu Ser Leu
        195                 200                 205

Asp Leu Ser Leu Asn Pro Met Asn Phe Ile Gln Pro Gly Ala Phe Lys
    210                 215                 220

Glu Ile Arg Leu His Lys Leu Thr Leu Arg Asn Asn Phe Asp Ser Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Gly Asn Leu Glu Lys Phe
            260                 265                 270

Asp Lys Ser Ala Leu Glu Gly Leu Cys Asn Leu Thr Ile Glu Glu Phe
        275                 280                 285

Arg Leu Ala Tyr Leu Asp Tyr Tyr Leu Asp Asp Ile Ile Asp Leu Phe
    290                 295                 300

Asn Cys Leu Thr Asn Val Ser Ser Phe Ser Leu Val Ser Val Thr Ile
305                 310                 315                 320

Glu Arg Val Lys Asp Phe Ser Tyr Asn Phe Gly Trp Gln His Leu Glu
                325                 330                 335

Leu Val Asn Cys Lys Phe Gly Gln Phe Pro Thr Leu Lys Leu Lys Ser
            340                 345                 350

Leu Lys Arg Leu Thr Phe Thr Ser Asn Lys Gly Gly Asn Ala Phe Ser
        355                 360                 365

Glu Val Asp Leu Pro Ser Leu Glu Phe Leu Asp Leu Ser Arg Asn Gly
    370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
                405                 410                 415

Asn Phe Leu Gly Leu Glu Gln Leu Glu His Leu Asp Phe Gln His Ser
            420                 425                 430

Asn Leu Lys Gln Met Ser Glu Phe Ser Val Phe Leu Ser Leu Arg Asn
        435                 440                 445

Leu Ile Tyr Leu Asp Ile Ser His Thr His Thr Arg Val Ala Phe Asn
    450                 455                 460

Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
                485                 490                 495

Asn Leu Thr Phe Leu Asp Leu Ser Gln Cys Gln Leu Glu Gln Leu Ser
            500                 505                 510

Pro Thr Ala Phe Asn Ser Leu Ser Ser Leu Gln Val Leu Asn Met Ser
        515                 520                 525

His Asn Asn Phe Phe Ser Leu Asp Thr Phe Pro Tyr Lys Cys Leu Asn
    530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575
```

```
Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
        595                 600                 605

Cys Ala Thr Pro Ser Asp Lys Gln Gly Met Pro Val Leu Ser Leu Asn
        610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
        675                 680                 685

Arg Asn Glu Leu Val Lys Asn Leu Glu Glu Gly Val Pro Pro Phe Gln
        690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
            740                 745                 750

Ile Ala Gln Thr Trp Gln Phe Leu Ser Ser Arg Ala Gly Ile Ile Phe
            755                 760                 765

Ile Val Leu Gln Lys Val Glu Lys Thr Leu Leu Arg Gln Gln Val Glu
770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
            820                 825                 830

Trp Gln Glu Ala Thr Ser Ile
            835
```

IMMUNOGENIC COMPOSITIONS AND METHODS FOR TREATING NEOPLASIA

CROSS-REFERENCE TO RELATED APPLICATIONS

This application is a continuation of PCT International Application No. PCT/US2011/034139 having an International filing date of Apr. 27, 2011, and is a continuation-in-part of PCT International Application No. PCT/US2010/052889 having an International filing date of Oct. 15, 2010. Each of PCT International Application Nos. PCT/US2011/034139 and PCT/US2010/052889 claims the benefit of U.S. Provisional Application No.: 61/328,471, filed Apr. 27, 2010. The entire contents of each of the foregoing applications are incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 21, 2013, is named 87185(71699)_SL.txt and is 17,010 bytes in size.

BACKGROUND OF THE INVENTION

Lethally irradiated tumor cell vaccines engineered to secrete GM-C SF (GVAX) showed promising efficacy in various models of melanoma, renal cell, prostate, and non-small cell lung, pancreatic, as well as head and neck squamous cell carcinoma, but due to the multiple immunological checkpoint blockades, GVAX as a monotherapy is unlikely to be clinically effective in advanced disease. GVAX was recently found to have uncertain efficacy in a phase III trial for advanced hormone refractory prostate cancer. The failure to overcome critical mechanisms of immune evasion by the tumor has been the major limitation of past immunotherapeutic strategies that were designed to primarily stimulate tumor-specific host immune responses. Among the many defined mechanisms for diminishing anti-tumor immune responses, regulatory T-cells (Treg), myeloid derived suppressor cells, and tolerizing dendritic cells (DCs) have been hypothesized as negative regulators that can prevent successful immunotherapy. One downstream consequence from some of these immune evasion checkpoint pathways is the limited number of activated antigen presenting cells (APCs) in the afferent arm of the immune system. Improved tumor cell vaccines that are able to overcome critical mechanisms of immune evasion by the tumor cell are needed.

SUMMARY OF THE INVENTION

As described below, the present invention generally features immunogenic compositions comprising neoplastic cells expressing a cytokine (GM-CSF) formulated with at least one TLR agonist and methods of using the composition to induce or enhance an immune response.

In one aspect, the invention generally features an immunogenic composition containing one or more proliferation-incompetent genetically modified neoplastic cells expressing a recombinant immune stimulatory cytokine and at least one Toll-like receptor (TLR) agonist.

In another aspect, the invention generally features a vaccine for ameliorating a neoplasia in a subject, the vaccine containing an effective amount of proliferation-incompetent neoplastic cells expressing a recombinant immune stimulatory cytokine and an effective amount of exogenous Toll-like receptor (TLR) agonist in a pharmaceutically acceptable excipient.

In yet another aspect, the invention generally features a method of inducing a neoplastic cell antigen-specific immune response in a subject having or having a propensity to develop a neoplasia, the method involving administering to the subject an effective amount of an immunogenic composition containing one or more proliferation-incompetent neoplastic cells expressing a recombinant immune stimulatory cytokine and comprising an exogenous Toll-like receptor (TLR) agonist in an amount sufficient to induce a neoplastic cell antigen-specific immune response in said subject.

In a further aspect, the invention generally features a proliferation-incompetent neoplastic cell comprising an expression vector encoding GM-CSF and at least one TLR agonist.

In yet another aspect, the invention generally features a method of treating or preventing a neoplasia in a subject having or having a propensity to develop a neoplasia, the method involving administering to the subject an effective amount of the immunogenic composition or vaccine described herein in an amount sufficient to induce a neoplastic cell antigen-specific immune response in said subject, thereby treating the subject.

In yet another aspect, the invention generally features a method of treating or preventing tumor progression or metastasis in a subject having a neoplasia, the method comprising administering to the subject an effective amount of any of the immunogenic compositions or vaccines described herein, thereby treating or preventing tumor progression or metastasis in the subject.

In yet another aspect, the invention generally features a method of treating an established tumor or preventing tumor formation in a subject, the method involving administering to the subject an effective amount of any of the immunogenic compositions or vaccines described herein, thereby treating an established tumor or preventing tumor formation in the subject.

In yet another aspect, the invention generally features a method of treating micrometastasis or residual disease in a subject having micrometastasis or residual disease, the method comprising administering to the subject an effective amount of any of the immunogenic compositions or vaccines described herein, thereby treating micrometastasis or residual disease in the subject.

In yet another aspect, the invention generally features a method of immunizing a subject, the method involving administering to the subject any of the immunogenic compositions or vaccines described herein.

In yet another aspect, the invention generally features a pharmaceutical composition for the treatment of neoplasia containing an effective amount of any of the immunogenic compositions or vaccines described herein and a pharmaceutically acceptable excipient.

In yet another aspect, the invention generally features a kit for the treatment of a neoplasia, the kit containing an effective amount of any of the immunogenic compositions or vaccines described herein, and directions for using the kit as in any of the methods described herein.

In yet another aspect, the invention generally features a method of treating or preventing cervical cancer in a subject, the method comprising administering to the subject an effective amount of any of the immunogenic compositions or vaccines described herein, thereby treating or preventing cervical cancer in the subject.

In yet another aspect, the invention generally features a method of treating polymorphic TLR deficiencies in a subject, the method comprising administering to the subject an effective amount of any of the immunogenic compositions or vaccines described herein, thereby treating the polymorphic TLR deficiencies in the subject.

In various embodiments of any of the above aspects or any other aspect of the invention delineated herein, the cytokine is granulocyte-macrophage colony-stimulating factor (GM-CSF). In another embodiment the cell contains comparable amounts of at least one TLR agonist and GM-CSF. In a further embodiment, the TLR agonist is a TLR4, TLR5, TLR6, TLR7 or TLR8, TLR9 agonist. In yet another embodiment the immunogenic composition contains a TLR4 agonist and a TLR7/8 agonist. In another embodiment the TLR4 agonist is LPS, an LPS fragment, or a synthetic glucopyranosyl lipid A analogue and the TLR7/8 analog is R848. In other embodiments the cells are rendered proliferation incompetent by irradiation. In certain embodiments the neoplastic cell is selected from the group consisting of leukemia, chronic myeloid leukemia, prostate cancer, head and neck, Squamous Cell Carcinoma, tongue cancer, larynx cancer, tonsil cancer, hypopharynx cancer, nasalpharynx cancer, breast cancer, colon cancer, lung cancer, melanoma, pancreatic cancer, glioblastoma and brain cancer. In other embodiments the composition comprises at least about 1 ng of TLR4 agonist per $1\times10^5$ cells-10 ng of TLR4 agonist per $1\times10^5$ cells. In further embodiments the composition contains at least about 3-5 ng per $5\times10^5$ cells. In another embodiment the cell contains a TLR agonist in association with Lipofectamine or other liposomal vectors. In further embodiments the cell contains LPS/liposomal micelles. In other embodiments the immongenic composition contains cells that express one or more tumor antigens. In further embodiments the immunogenic composition contains cells that are autologous or allogeneic.

In various embodiments of any of the above aspects or any other aspect of the invention delineated herein, the neoplastic cell is derived from a cancer cell line or is derived from a tumor. In another embodiment the cancer cell line or tumor is selected from leukemia, chronic myeloid leukemia, prostate cancer, head and neck, Squamous Cell Carcinoma, tongue cancer, larynx cancer, tonsil cancer, hypopharynx cancer, nasalpharynx cancer, breast cancer, colon cancer, lung cancer, melanoma, pancreatic cancer, glioblastoma and brain cancer. In another embodiment the immunogenic composition is administered systemically or locally. In further embodiments the immunogenic composition is administered by intramuscular injection, intravenous injection, intratumoral injection, or peritumoral injection. In additional embodiments the methods involve administering to the subject an effective amount of one or more chemotherapeutics. In certain embodiments the one or more chemotherapeutics is selected from abiraterone acetate, altretamine, anhydrovinblastine, auristatin, bexarotene, bicalutamide, BMS184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly- l-Lproline-t-butylamide (SEQ ID NO: 1), cachectin, cemadotin, chlorambucil, cyclophosphamide, 3',4'-didehydro-4'-deoxy-8'-norvin- caleukoblastine, docetaxol, doxetaxel, cyclophosphamide, carboplatin, carmustine (BCNU),cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine. In additional embodiments the methods enhance activation of dendritic cells and/or increases the number of AH1-specific cytotoxic T-cells or p15E-specific cytotoxic T-cells relative to the use of GVAX alone. In certain embodiments the methods reduce or stabilize tumor cell proliferation, tumor growth, or subject survival relative to the use of GVAX alone. In further embodiments the cell is derived from a leukemia, chronic myeloid leukemia, prostate cancer, head and neck, Squamous Cell Carcinoma, tongue cancer, larynx cancer, tonsil cancer, hypopharynx cnacer, nasalpharynx cancer, breast cancer, colon cancer, lung cancer, melanoma, pancreatic cancer, glioblastoma and brain cancer or a cell line thereof. In additional embodiments the cell comprises a TLR4 and a TLR7/8 agonist. In other embodiments the TLR agonist is in association with liposomal vector.

Definitions

By "cytokine" is meant a hormone that acts locally and that modulates an individual's immune response.

By "genetically modified neoplastic cell" is meant a cell or a population of cells that has been genetically modified to express a transgene, and that is administered to a patient as part of cancer therapy. An immunogenic composition or vaccine of the invention comprises neoplastic (e.g., tumor) cells that are "autologous" or "allogeneic" to the patient undergoing treatment or "bystander cells" that are mixed with tumor cells taken from the patient. Generally, the genetically modified neoplastic cell is of the same general type of tumor cell as is afflicting the patient. For example, a patient suffering from melanoma will typically be administered a genetically modified cell derived from a melanoma. A GM-CSF-expressing genetically modified tumor cell vaccine may be referred to herein as "GVAX". Autologous and allogeneic cancer cells that have been genetically modified to express a cytokine, e.g., GM-CSF, followed by readministration to a patient for the treatment of cancer are described in U.S. Pat. Nos. 5,637,483, 5,904,920, 6,277,368 and 6,350,445, as well as in US Patent Publication No. 20100150946, each of which is expressly incorporated by reference herein. A form of GM-CSF-expressing genetically modified cancer cells or a "cytokine-expressing cellular vaccine" for the treatment of pancreatic cancer is described in U.S. Pat. Nos. 6,033,674 and 5,985,290, both of which are expressly incorporated by reference herein. A universal immunomodulatory cytokine-expressing bystander cell line is described in U.S. Pat. No. 6,464,973, expressly incorporated by reference herein.

By "Granulocyte-macrophage colony stimulating factor (GM-CSF) polypeptide" is meant a cytokine or fragment thereof having immunomodulatory activity and having at least about 85% amino acid sequence identity to GenBank Accession No. AAA52122.1.

An exemplary GM-CSF sequence (NCBI AAA52122.1) is provided below:

```
  1 mwlqsllllg tvacsisapa rspspstqpw ehvnaiqear rllnlsrdta aemnetvevi
 61 semfdlqept clqtrlelyk qglrgsltkl kgpltmmash ykqhcpptpe tscatqiitf
121 esfkenlkdf llvipfdcwe pvqe (SEQ ID NO: 2)
```

GM-CSF has been shown to induce the growth of hematopoietic cells of granulocyte and macrophage lineages. In addition, it also activates the antigen processing and presenting function of dendritic cells, which are the major antigen presenting cells (APC) of the immune system. In one embodiment, an immunogenic composition comprises a GM-CSF coding sequence operatively linked to regulatory elements for expression in the cells of the vaccine.

By "GM-CSF nucleic acid molecule" is meant a polynucleotide encoding a GM-CSF polypeptide.

A GM-CSF nucleic acid molecule may encode a murine or human GM-CSF and may be in the form of genomic DNA (See, US Patent Publication NO. 2006/0057127, which is hereby incorporated by reference in its entirety) or cDNA (See US Patent Publication NO. 2006/0057127, which is hereby incorporated by reference in its entirety). In one embodiment, the GM-CSF coding sequence encodes the amino acid sequence described in US Patent Publication NO. 2006/0057127, which is hereby incorporated by reference in its entirety. Other examples of GM-CSF coding sequences are found in Genbank accession numbers:AF373868, ACO34228, ACO34216, M 10663 and NM000758.

An exemplary GM-CSF coding sequence (AF373868) is provided below:

```
   1 gcagtctgtt tcctaccaga ctgggagcct caagggccaa atgtgagggc cagtgggagg
  61 gtcccgttta cctccccaga acaggtcctg gtgtggattg gaaagacttg ttgactgact
 121 gtctgagcta tgacaactca tttctaggag gaaagtgacc ttctctccca gatgggtcat
 181 acaggctctc tgcctccctg gccatcagct gaaccactat ctatggctcc cttccctgcc
 241 ctccagcctc cagggtgcta tccaacacat gtgatatcta catgtagtat ccatgtcctc
 301 atctctcccc cgagagctcc ctggaaagag ctgagccaag gccttgcaaa aaaggtggag
 361 aaagggccag ggcctggaca tttcatgttc ccaccccagc ctggccacta ggagtgttct
 421 acgcaggctc agatggatgg ggctggcctc acagtggggt ctggaggact aaggtttggt
 481 ttctctatgc aaggtcagaa aaactcccac agtacaggga aactggccag ggctgcagac
 541 tcagaccaca gtgctaaagc catgaactcc acctgctctc tgaaggctcg ccaacctgag
 601 tccagcagaa tgttctcgct tgtgtccaac cccactggtt taggctgaat cagcctctag
 661 ggcccagagg cactgcacct ggagtaggga gcttctccag tatcagagtc accttcagag
 721 gcctggagcc tttcataaag caggtaagag gactcaatag atgcatctgc atggaaaaca
 781 tcctcccctc taccaggcac ctgtatgtac aaccaatcac agcagcacac atacacccag
 841 aaatgggcac gtgtgggccc acaccccttt agctatgaaa cccaggcatg gggcagcttg
 901 agccagatac cttgtgcaaa cacaaactcg tgctgtcttc tctgaactcc attgtgaaaa
 961 tcaaacactt gtcagcccct caagagcctt tagatttcct acttccacac ttccacagaa
1021 aggcctctgg agttggggga tgctggggtt atgtaggaaa ttaagcctgg agggccttgc
1081 tggggaagcc attgtccctg tacctgagat ggatgcagcc acagccctgg agccagcctg
1141 aagctcctgg tgtcttctgg gggctacata taggagtgta gtccgaacct cagaggggca
1201 aacctgctct gcagagggaa tcaaggttca cataaccaga gagggagtc actcaggaag
1261 gtggctccag agccaagagt cagactctgg gtcccgactt gacccagcca cacccctct
1321 gaagcttgct gagagtggct gcagtctcgc tgctggatgt gcacatggtg gtcattccct
1381 ctgctcacag gggcagggt ccccccttac tggactgagg ttgcccctg ctccaggtcc
1441 tgggtgggag cccatgtgaa ctgtcagtgg ggcaggtctg tgagagctcc cctcacactc
1501 aagtctctca cagtggccag agaagaggaa ggctggagtc agaatgaggc accagggcgg
1561 gcatagcctg cccaaaggcc cctgggatta caggcaggat ggggagccct atctaagtgt
1621 ctcccacgcc ccaccccagc cattccaggc caggaagtcc aaactgtgcc cctcagaggg
1681 aggggcagc ctcaggccca ttcagactgc caggggaggg ctggagagcc ctcaggaagg
1741 cgggtgggtg ggctgtcggt tcttggaaag gttcattaat gaaacccccc aagcctgacc
1801 acctagggaa aaggctcacc gttcccatgt gtggctgata agggccagga gattccacag
1861 ttcaggtagt tcccccgcct ccctggcatt ttgtggtcac cattaatcat ttcctctgtg
1921 tatttaagag ctcttttgcc agtgagccca gtacacagag agaaaggcta aagttctctg
```

-continued

```
1981 gaggatgtgg ctgcagagcc tgctgctctt gggcactgtg gcctgcagca tctctgcacc
2041 cgcccgctcg cccagcccca gcacgcagcc ctgggagcat gtgaatgcca tccaggaggc
2101 ccggcgtctc ctgaacctga gtagagacac tgctgctgag atggtaagtg agagaatgtg
2161 ggcctgtgcc taggccaccc agctggcccc tgactggcca cgcctgtcag cttgataaca
2221 tgacattttc cttttctaca gaatgaaaca gtagaagtca tctcagaaat gtttgacctc
2281 caggtaagat gcttctctct gacatagctt tccagaagcc cctgccctgg ggtgaggtg
2341 gggactccat tttagatggc accacacagg gttgtccact ttctctccag tcagctggct
2401 gcaggaggag ggggtagcaa ctgggtgctc aagaggctgc tggccgtgcc cctatggcag
2461 tcacatgagc tcctttatca gctgagcggc catgggcaga cctagcattc aatggccagg
2521 agtcaccagg ggacaggtgg taaagtgggg gtcacttcat gagacaggag ctgtgggttt
2581 ggggcgctca ctgtgccccg agaccaagtc ctgttgagac agtgctgact acagagaggc
2641 acagagggggt tcaggaaca acccttgccc acccagcagg tccaggtgag gcccacccc
2701 cctctccctg aatgatgggg tgagagtcac ctccttccct aaggctgggc tcctctccag
2761 gtgccgctga gggtggcctg ggcggggcag tgagaagggc aggttcgtgc ctgccatgga
2821 cagggcaggg tctatgactg gacccagcct gtgcccctcc caagccctac tcctgggggc
2881 tgggggcagc agcaaaaagg agtggtggag agttcttgta ccactgtggg cacttggcca
2941 ctgctcaccg acgaacgaca ttttccacag gagccgacct gcctacagac ccgcctggag
3001 ctgtacaagc agggcctgcg gggcagcctc accaagctca agggccctt gaccatgatg
3061 gccagccact acaagcagca ctgccctcca accccgtga gtgcctacgg cagggcctcc
3121 agcaggaatg tcttaatcta gggggtgggg tcgacatggg gagagatcta tggctgtggc
3181 tgttcaggac cccagggggt ttctgtgcca acagttatgt aatgattagc cctccagaga
3241 ggaggcagac agcccatttc atcccaagga gtcagagcca cagagcgctg aagcccacag
3301 tgctccccag caggagctgc tcctatcctg gtcattattg tcattatggt taatgaggtc
3361 agaggtgagg gcaaacccaa ggaaacttgg ggcctgccca aggcccagag gaagtgccca
3421 ggcccaagtg ccaccttctg gcaggacttt cctctggccc cacatggggt gcttgaattg
3481 cagaggatca aggaagggag gctacttgga atggacaagg acctcaggca ctccttcctg
3541 cgggaaggga gcaaagtttg tggccttgac tccactcctt ctgggtgccc agagacgacc
3601 tcagcccagc tgccctgctc tgccctggga ccaaaaaggc aggcgtttga ctgcccagaa
3661 ggccaacctc aggctggcac ttaagtcagg cccttgactc tggctgccac tggcagagct
3721 atgcactcct tggggaacac gtgggtggca gcagcgtcac ctgacccagg tcagtgggtg
3781 tgtcctggag tgggcctcct ggcctctgag ttctaagagg cagtagagaa acatgctggt
3841 gcttccttcc cccacgttac ccacttgcct ggactcaagt gttttttatt tttctttttt
3901 taaaggaaac ttcctgtgca acccagatta tcacctttga aagtttcaaa gagaacctga
3961 aggactttct gcttgtcatc ccctttgact gctgggagcc agtccaggag tgagaccggc
4021 cagatgagc tggccaagcc ggggagctgc tctctcatga acaagagct agaaactcag
4081 gatggtcatc ttggagggac caagggggtgg gccacagcca tggtgggagt ggcctggacc
4141 tgccctgggc cacactgacc ctgatacagg catggcagaa gaatgggaat atttatact
4201 gacagaaatc agtaatattt atatatttat atttttaaaa tatttattta tttatttatt
4261 taagttcata ttccatattt attcaagatg ttttaccgta ataattatta ttaaaaatat
4321 gcttctactt gtccagtgtt ctagtttgtt tttaaccatg agcaaatgcc agtggtgcct
```

-continued
```
4381 gccttcccat gaggcagggg agggaggaaa cggggaggtg gagaggggggc ggggggcctcc 4441 caggcgttgg gcactatcca agggccaaca ctgtcagagc agaggggagg tgagagccgg 4501 gcataggtgc ggaattctgc acacctggac gggcttcccg ggatgctcca gggctcccac 4561 cccagagaat ggctctcaag ttcacctgga agtccaagtg accagcccag ggaactctta 4621 tcccagagaa gggcaccacc cttcctgggg aggcctgggg gttggctggt cactggctga 4681 acaggcccac tctggcatca ggcaaaacac ctgccctgta gaggccttgg ccctgtgcc 4741 ccacgccctg cccctcacac tctgagattt aaccattccg aaagtaaaca gcaaaataga 4801 ctaactgttc aggggaaaag aaaccaaacc acagggtca cagtgcagcg tatttaccaa 4861 acttgcccca aaatgggtga tcttaatctc tgagagtcag aatgtaaggt cataatttgt 4921 tggtacatgg ctgtagtgcc gcatgtttct gaattggttt ttattttttac atgaaatttt 4981 gaatctaatc aggcactttc ccctaaaact catggcctgc aggctaaaaa caaagtaggc 5041 ctcctccttc tccttacttt gacagctggg ctcaaggcct tgttcctgaa cctgttccct 5101 catctccctc caggactatg aggaagtgga tgtgccccaa gtcttaggcg ggcagcaggg 5161 ccagcttctc cttgacaggt gggcctaagg aagctggctt gtggcagctt tagccctgc 5221 ctggcactgt ctgcagtcat gcgcccacca ccctcttgc ttcctctact tcagtcagca 5281 cctgcagaca gcgccaggcc tggccagaga cccactccat gctcatgcag aaagaccgtg 5341 acttcaggtg tgattacaaa taagaagtca gggtgaacgc tcaggatgaa gcctgagtgt 5401 cagcacaggc aagaatccat gaagtgtgct gtggttgttg aaaatgcatg aaaatcacat 5461 cttgcccagc gataaggtcc tctctgtctt ccgcgtaagc cagtgatgac tgataagagg 5521 tttagcattt ccttagcctc acatatatag gtaccctct ccacagaaat gctgccaagc 5581 ccagggctcg gaccagcttg gagtcacctt caagtaatac catgcacctg tacgtgctcc 5641 tggctcatgt gctctggggg tcagaaagcc attcttccca atgaaagtag ccacgatatc 5701 tccccacgaa aagtacacag cagtctgtgc tgacattcag aaagaactct cggctgacaa 5761 taacacacac aagataagtc tgggtctcca tcaaacgtta ttttgctctt agtgcccctt 5821 tgtgctcctg accaatttct ctggcttccg gggtcccttc aataggcccc agaaaaccag 5881 tgaggtaaga aacagctgcc ccgggacctt tcataccaca tttgaacagg gagagagaga 5941 tctcaccagt cagtgcccag ggaagagata acaacaaggg atagtggagt ga
(SEQ ID NO: 3)
```

By "Toll-like receptor agonist" is meant an agent that activates a member of the TLR receptor family.

By "glucopyranosyl lipid A" or "glycopyranosyl lipid A" or "glycopyranosyl lipid adjuvant" or "GLA" is meant a novel, clinical-stage, human toll-like receptor-4 (TLR-4) agonist which is described in U.S. patent application Ser. No. 11/862,122 and U.S. Patent Application Publication No. 20080131466 which are incorporated herein in their entirety.

By "IDC-1005" is meant a mixture of 1 mg/ml GLA and 0.2 mg/ml R848 in the presence of a stable squalene oil-in water emulsion that contains phosphatidylcholine.

By "liposomal vector" is meant any composition that can be used to deliver agents to cells through formation of liposomes, a non-limiting example of which is lipofectamine.

By "R848" is meant an imidazoquinoline compound with a molecular weight of 314.17 which is a TLR agonist that activates immune cells via the TLR7/TLR8 MyD88-dependent signaling pathway. R848 has the following formula: $C_{17}H_{22}N_4O_2$; and structure:

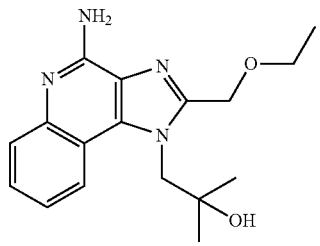 [SMILES: CCOCc1nc2c(N)nc3ccccc3c2n1CC(C)(C)O]

By "TEGVAX" is meant a GVAX further formulated with a TLR agonist.

By "Toll like receptor (TLR)" is meant a member of the Toll-like receptor family of proteins or a fragment thereof that senses a microbial product and/or initiates an adaptive immune response. In one embodiment, a TLR activates a dendritic cell (DC).

By "Toll like receptor 4 (TLR4)" is meant a polypeptide having at least 85% sequence identity to NP_612564, or a fragment thereof having and having immunomodulatory activity. The sequence of human toll-like receptor 4 precursor NP_612564 is provided below:

```
  1 mmsasrlagt lipamaflsc vrpeswepcv evvpnityqc melnfykipd nlpfstknld
 61 lsfnplrhlg sysffsfpel qvldlsrcei qtiedgayqs lshlstlilt gnpiqslalg
121 afsglsslqk lvavetnlas lenfpighlk tlkelnvahn liqsfklpey fsnitnlehl
181 dlssnkiqsi yctdlrvlhq mpllnlsldl slnpmnfiqp gafkeirlhk ltlrnnfdsl
241 nvmktciqgl aglevhrlvl gefrnegnle kfdksalegl cnltieefrl ayldyylddi
301 idlfncltnv ssfslvsvti ervkdfsynf gwqhlelvnc kfgqfptlkl kslkrltfts
361 nkggnafsev dlpslefldl srnglsfkgc csqsdfgtts lkyldlsfng vitmssnflg
421 leqlehldfq hsnlkqmsef svflslrnli yldishthtr vafngifngl sslevlkmag
481 nsfqenflpd iftelrnltf ldlsqcqleq lsptafnsls slqvlnmshn nffsldtfpy
541 kclnslqvld yslnhimtsk kqelqhfpss laflnitqnd factcehqsf lqwikdqrql
601 lvevermeca tpsdkqgmpv lslnitcqmn ktiigvsvls vlvvsvvavl vykfyfhlml
661 lagcikygrg eniydafviy ssqdedwvrn elvknleegv ppfqlclhyr dfipgvaiaa
721 niihegfhks rkvivvvsqh fiqsrwcife yeiaqtwqfl ssragiifiv lqkvektllr
781 qqvelyrlls rntyleweds vlgrhifwrr lrkalldgks wnpegtvgtg cnwqeatsi
(SEQ ID NO: 4)
```

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. Patent law and can mean " includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "disease" is meant any condition or disorder that damages or interferes with the normal function of a cell, tissue, or organ.

By "effective amount" is meant an amount sufficient to induce or enhance an immune response against a neoplastic cell or specific to a tumor antigen, to reduce or stabilize tumor growth, to enhance subject survival, or to otherwise ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids. In one embodiment, a fragment of a TLR4 agonist comprises at least about 10, 25, 50, 100, 150, 200, 250, 300, 400, 500, 600 or 700 amino acids of LPS or another TLR4 agonist that is sufficient to enhance an immune response in a subject.

"Hybridization" means hydrogen bonding, which may be Watson-Crick, Hoogsteen or reversed Hoogsteen hydrogen bonding, between complementary nucleotide bases. For example, adenine and thymine are complementary nucleotide bases that pair through the formation of hydrogen bonds.

By "isolated" is meant a material that is free to varying degrees from components which normally accompany it as found in its native state. "Isolate" denotes a degree of separation from original source or surroundings.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "micrometastasis" is meant a form of metastasis in which secondary tumors are too minuscule to be clinically detected.

By "minimal residual disease" is meant the small numbers of tumor cells that remain in the patient during treatment or after treatment.

By "neoplasia" is meant a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasias can affect a variety of cell types, tissues, or organs, including but not limited to an organ selected from the group consisting of bladder, bone, brain, breast, cartilage, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasias include cancers, such as sarcomas, carcinomas, or plasmacytomas (malignant tumor of the plasma cells).

Neoplasia cells that invade surrounding tissue or enter the bloodstream or lymphatic vessels form secondary tumors, or metastases, at a distance from the original tumor. Neoplasia that has metastasized is more difficult to treat and often has a poorer prognosis. Depending on the severity of the neoplasia (i.e., tumor size and invasiveness), a stage number is assigned, I, II, III, or IV. Stage I neoplasias are the least advanced and have the best prognosis. Stage II neoplasias typically include larger tumors and are associated with a somewhat poorer prognosis. Stage III and IV neoplasias have spread beyond their sites of origin and have the poorest prognosis.

As used herein, "obtaining" as in "obtaining an agent" includes synthesizing, purchasing, or otherwise acquiring the agent.

As used herein, "recombinant" includes reference to a polypeptide produced using cells that express a heterologous polynucleotide encoding the polypeptide. The cells produce the recombinant polypeptide because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, under-expressed or not expressed at all.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

A "tumor," as used herein, refers to all neoplastic cell growth and proliferation, whether malignant or benign, and all precancerous and cancerous cells and tissues.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1 shows the delivery of TLR4 agonist into GVAX. FIG. 1 is a set of FACS graphs showing the delivery of TLR4 agonists into GVAX. To optimize the absorption efficiency of LPS into the GVAX vaccine cells, the concentrations of Lipofectamine and LPS-BODIPY fluorophore conjugate were varied as noted. Cells were washed 5 times prior to the flow cytometry analysis. LPS was undetectable in the final wash using the LAL assay to less than 0.125 EU/ml. Optimal absorption was at 6 hr incubation with 40 μg/ml of Lipofectamine and 25 μg/ml of LPS per $1\times10^5$ cells. These conditions were used for quantitation of LPS on a per cell basis.

FIGS. 2A, 2B, and 2C show that TEGVAX can induce an anti-tumor response in vivo. B16 inoculated C57BL/6 (FIG. 2A), SCCFVII/SF inoculated C3H (FIG. 2B), and CT26 inoculated Balb/c (FIG. 2C) mice were treated with appropriate PBS, GVAX, or TEGVAX peritumorally typically from 3-5 days after the tumor injection. In vivo tumor progression in the TEGVAX group in all the murine models studied was statistically slower than those in the GVAX group. For the B16 and the SCCFVII/SF models, there were no differences between GVAX treated group and the PBS treated group. In the CT26 model, 40-60% of the mice in the TEGVAX group experienced a regression of their palpable tumor to undetectable levels by day 18. Equimolar LPS formulated into 293T cells also showed no difference in growth rate in comparison to control treated mice. Mice that showed regression of tumor were rechallenged with CT26 tumor ($2\times10^6$) and no tumor growth were noted. In all three murine models, the reduced tumor growth rate correlated with enhanced survival for mice in the TEGVAX group compared to those in the GVAX group.

FIG. 4A is a set of photomicrographs of the immunohistochemical staining of CD4+, CD8+, CD86+, and CD45+ cells in CT26 tumor treated with control, GVAX, or TEGVAX. The yellow cells represent the co-localized staining of CD4 or CD8 with CD45 in the first two panels. The third panel represents CD86 conjugate staining alone. These cells were formally quantitated in 10 randomly selected fields per slice at 40× magnification. FIG. 4B is a graphical presentation of the quantitated data obtained by immunohistochemistry. Within the tumor treated with either GVAX or TEGVAX there were statistical differences in each of quantitated CD4, CD8, CD86 and CD45 cells between the two groups ($P<0.01$).

FIG. 6A is a graph of the number of AH1 specific IFN-producing T-cells were statistically greater in the TEGVAX group compared to GVAX group in both the spleen and the draining LN ($P<0.01$). FIG. 6B is a graph of AH1 specific CTL killing. In vivo CTL assays were used to measure percent killing of AH1 specific CTLs in CT26 tumor bearing mice treated with or without TEGVAX.-gal CFSE labeled low and AH1 CFSE labeled high cells were co-injected into naïve, tumor bearing or TEGVAX treated tumor bearing groups. The average mean specific tumor lysis was higher in the TEGVAX group compared to the untreated groups ($P<0.07$).

FIG. 11A and FIG. 11B provide several panels showing results of an ELISPOT assay (FIG. 11A) and in vivo CTL assay (FIG. 11B) showing that mice treated with GVAX/GLA/R848 had the highest number of p15E-specific T-cells, and that this result correlated with the in vivo tumor growth rate. Mice treated with the vaccine formulations were harvested 1-2 weeks after treatment, and their spleen analyzed for tumor specific T-cells.

FIG. 13A and FIG. 13B provide FACS analysis showing that GVAX/GLA/R848 treated mice had statistically significant numbers of CD11c+cells that express IL-12.

DETAILED DESCRIPTION OF THE INVENTION

Figure 3:
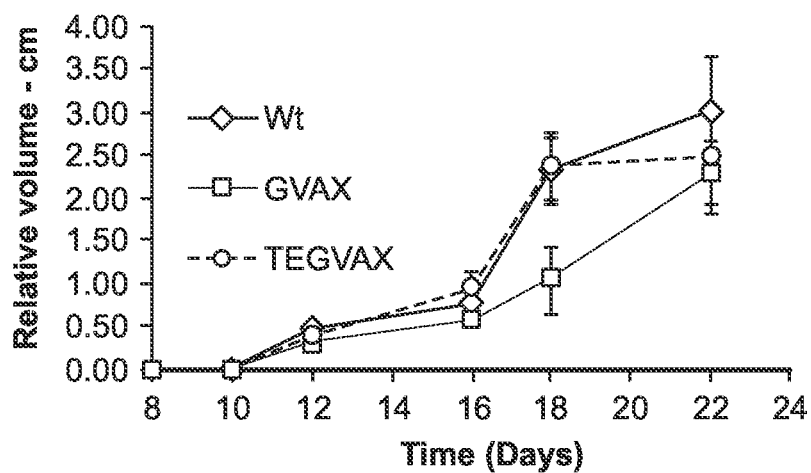
FIG. 3 shows that the improved in vivo anti-tumor response noted for TEGVAX is MyD88 dependent. Using the B16 model, the in vivo tumor growth rate was performed with MyD88 null mice with the vaccine treatment performed intratumorally 3-5 day s after tumor inoculation. The anti-tumor response in the TEGVAX treated group is abrogated in MyD88 null mice.

The invention provides immunogenic compositions comprising neoplastic cells expressing a cytokine (GM-CSF) formulated with at least one TLR agonist and methods of using the composition to induce or enhance an immune response.

The invention is based, at least in part, on the discovery that the addition of TLR agonists to a tumor cell-based vaccine increased the efficacy of the vaccine by overcoming host immune response avoidance mechanisms present in the tumor tissue. In particular, as reported in more detail below, a syngeneic GM-CSF secreting whole cell tumor vaccine (GVAX) with TLR4 agonist (TEGVAX for TLR-enhanced GVAX) was generated. The efficacy of this vaccine was tested in three different therapeutic murine models, including the poorly immunogenic B16 murine melanoma model. Immunohistochemistry, flow cytometry analysis, ELISPOT, and in vivo CTL analysis was utilized to assess both innate and adaptive immune response against the tumor tissue. The intratumoral and systemic administration of TEGVAX resulted in an increased antitumor response in vivo in comparison to GVAX alone. Improved antitumor efficacy of TEGVAX was not present in TLR signaling impaired MyD88−/− mice. In the CT26 murine model in Balb/c mice, 40-60% of the mice showed regression of the transplanted tumor. When rechallenged with CT26 tumor cells, these mice proved to be immunized against the tumor. TEGVAX treated tumors showed increased infiltrating CD4 and CD8 T-cells as well as increased numbers of CD86+ cells in the tumor tissue. Draining lymph nodes from the TEGVAX treated mice had enhanced number of activated CD86+MHCII+ and CD80+ MHCII+ dendritic cells in comparison to GVAX and mock treated groups. ELISPOT assay as well as in vivo CTL assay showed increased numbers of CTLs specific for the AH1 tumor antigen in mice treated with TEGVAX. Cell based vaccine can be formulated with TLR agonist with improved anti-tumor response in vivo.

TLR Agonists Enhance Antitumor Immune Responses

Use of tumor cell vaccines as a source of unbiased tumor antigens have shown to be safe in multiple clinical trials. However, the clinical efficacy of this approach has been limited by its modest upregulation of activated antigen presenting cells that can skew the T-cell response towards an antitumor cytotoxic response. In the context of infection, TLR agonists have been shown to render dendritic cell activation immunogenic, whereas lack of TLR4 signaling can lead to tolerance(14). Blander and Medzhitov showed phagocytosed microbial antigens can be more efficiently presented in the presence of LPS(17). Without TLR4 signaling in the antigen-containing phagolysosome, peptide-MHC class II complexes are inefficiently presented on the cell surface on DCs. The implication from these studies is that localized TLR4 stimulation can enhance antitumor response when given as part of a combinatorial vaccine.

One concern for using any TLR agonists is its toxicity since the physiologic ligand for TLR4 is LPS, the macromolecule responsible for sepsis. TLR4 agonist activity of LPS has been isolated to the lipid A component of LPS, and various forms of non-toxic lipid A forms have been introduced into cancer patients(18). Others have used LPS at suprapyrogenic doses intradermally for cancer patients without any evidence of sepsis and anaphylaxis(19). Another concern is that TLR4 receptors expressed on tumor cells may promote carcinogenesis(20).

The GVAX vaccine, which comprises genetically modified tumor cells expressing the immunomodulatory cytokine GM-CSF, is currently undergoing clinical trials for melanoma, breast, pancreatic, and colon cancer. As reported herein, combining TLR stimulation locoregionally with GVAX can significantly enhance the immunogenicity of the GVAX vaccine. To minimize pro-carcinogenic TLR4 stimulation and to minimize systemic TLR4 stimulation, LPS and other TLR agonists have been formulated into GVAX cells, and this novel combinatorial vaccine showed anti-tumor efficacy in several murine models.

Accordingly, the invention provides therapeutic compositions comprising TLR agonist containing neoplasia cell-based vaccines, and methods of using such cell-based vaccines to prevent, reduce, or eliminate the invasiveness of neoplastic cells (e.g., breast cancer and melanoma cells) or to otherwise treat a neoplasia or symptom thereof.

In one particular embodiment, the invention provides an autologous cancer cell vaccine consisting of patient-specific cancer cells genetically modified to secrete granulocyte-macrophage colony stimulating factor (GM-CSF) and further formulated to comprise a toll like receptor agonist. GM-CSF modulates the proliferation and differentiation of a variety of hematopoietic progenitor cells with some specificity towards stimulation of leukocyte production and may reverse treatment-induced neutropenias. This agent also promotes antigen presentation, up-regulates antibody-dependent cellular cytotoxicity (ADCC), and increases interleukin-2-mediated lymphokine-activated killer cell function and may augment host antitumoral immunity. TLR agonists act as adjuvants and increase the efficacy of the vaccine. Tumor cell-based vaccines formulated with TLR agonists increased the number of activated locoregional dendritic cells as well as increasing the tumor specific CTL response. For safety, cells are irradiated prior to vaccination.

Immunogenic Compositions

Immunogenic compositions of the invention, including cancer vaccines, are useful as therapeutics and prophylactics for the treatment of specific types of cancers. Advantageously, these vaccines may be tailored to treat the cancers of particular individuals, by generating vaccines that target specific tumor antigens expressed on a tumor in a subject. Vaccines of the invention typically contain inactivated tumor cells or cells expressing tumor antigens that have been genetically modified to express GM-CSF, the cells further comprise a TLR4 agonist or fragment thereof. Cells of the invention are induced to take up the TLR4 agonist by contacting them with the TLR4 agonist in combination with Lipofectamine or other liposomal vehicles, for example, oil/water emulsion lipophilic molecules, anything that would solubilize these lipophilic molecule, non-cytotoxic, passive absorption. Without wishing to be bound by theory, the TLR agonist, or a biologically active fragment thereof, is contacted with liposome under conditions sufficient to form TLR agonist-containing micelles. The micelles are absorbed non-specifically up by the GM-CSF expressing tumor cells and this TLR agonist formulated cellular vaccine may be used to stimulate a subject's immune system. In other embodiments, TLR agonists are adsorbed onto cells in the presence of a vehicle. One non-limiting example of a suitable vehicle is a stable squalene oil-in water emulsion (e.g., a 10% by weight oil in water emulsion) that contains phosphatidylcholine. The immune system responds to this stimulation by generating immunoresponsive cells that target the neoplasia. In particular embodiments, cancer vaccines of the invention desirably target undetectable tumor cells, such as micrometastasis or residual disease, thereby preventing relapses of the neoplasia. Unlike vaccines for other disease that prevent the occurrence of the disease, cancer vaccines are typically administered after a subject has been identified as having a neoplasia.

Neoplastic cell vaccines are produced using the cellular compositions of the invention, which are generated as described herein. The cells are rendered proliferation-incompetent and injected into the patient where the tumor initiating cell antigens stimulate an immune response. Desirably, the immune system targets the small population of cancer cells that carry one or more antigens that was displayed on the lethally irradiated cells.

Recombinant Polypeptide Expression

The invention provides cells that have been genetically modified to express a recombinant GM-CSF polypeptide. GM-CSF polypeptides of the invention are produced using virtually any method known in the scientific community. Typically, recombinant polypeptides are produced by transformation of a suitable host cell (e.g., a cell derived from a tumor or a neoplastic cell line) with all or part of a GM-CSF polypeptide-encoding nucleic acid molecule or fragment thereof in a suitable expression vehicle. Such nucleic acid molecules can be delivered to cells derived from a subject having a neoplasia or to a neoplastic cell line in vitro. The nucleic acid molecules must be delivered to the cells of a subject in a form in which they can be taken up so that therapeutically effective levels of a GM-CSF protein or fragment thereof can be produced.

Transducing viral (e.g., retroviral, adenoviral, and adeno-associated viral) vectors can be used for gene delivery, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding a GM-CSF protein, variant, or a fragment thereof, can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346). Most preferably, a viral vector is used to administer a GM-CSF polynucleotide to a cell of the invention, prior to, concurrent with, or following the delivery of a TLR4 agonist to the cell.

Non-viral approaches can also be employed for the introduction of a vector encoding GM-CSF to a cell derived from a patient having a neoplasia or derived from a neoplastic cell line. For example, a nucleic acid molecule encoding GM-CSF can be introduced into a cell by administering the nucleic acid molecule in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the nucleic acids are administered in combination with a liposome and protamine. The cells may be treated with Lipofectamine in combination with a TLR4 agonist concurrently, prior to, or following transfection with the GM-CSF encoding vector.

Methods for accomplishing transfection in vitro include the use of calcium phosphate, DEAE dextran, electroporation, and protoplast fusion. Liposomes can also be potentially beneficial for delivery of DNA into a cell.

cDNA expression for use in the methods of the invention can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Another therapeutic approach included in the invention involves administration of a recombinant therapeutic, such as a cell secreting a recombinant GM-CSF protein, variant, or fragment thereof, either directly to the site of a potential or actual disease-affected tissue (e.g., intertumorally, peritumorally) or systemically (for example, by any conventional recombinant protein administration technique). The dosage of the administered cells expressing the GM-CSF protein depends on a number of factors, including the size and health of the individual patient. For any particular subject, the specific dosage regimes should be adjusted over time according to the individual need and the professional judgment of the person administering or supervising the administration of the compositions.

Autologous Cells

The use of autologous genetically modified cells expressing a cytokine, e.g. GM-CSF and comprising a TLR4 antigen, provide advantages since each patient's tumor expresses a unique set of tumor antigens that can differ from those found on histologically-similar, MHC-matched tumor cells from another patient. See, e.g., Kawakami et al., J. Immunol., 148, 638-643 (1992); Darrow et al., J. Immunol., 142, 3329-3335 (1989); and Hom et al., J. Immunother., 10, 153-164 (1991). In contrast, MHC-matched tumor cells provide the advantage that the patient need not be taken to surgery to obtain a sample of their tumor for genetically modified tumor cell production.

In one embodiment, the method of treating a subject having a neoplasia involves obtaining tumor cells from the subject; contacting the cells with an expression vector encoding GM-CSF; contacting the cells with a TLR agonist under conditions that provide for the cell to phagocytose or otherwise take up the TLR agonist; rendering the cells proliferation incompetent (e.g., by irradiating the cells); and administering the cells to the subject from which they were obtained. Preferably, the composition is administered intradermally, subcutaneously or intratumorally to the mammalian subject.

In some cases, a single autologous tumor cell may express GM-CSF alone or GM-CSF in combination with one or more tumor-associated antigens. In other cases, GM-CSF and the one or more tumor-associated antigens may be expressed by different autologous tumor cells. In one aspect of the invention, an autologous tumor cell is modified by introduction of a vector comprising a nucleic acid sequence encoding GM-CSF, operatively linked to a promoter and expression/control sequences necessary for expression thereof. In another aspect, the same autologous tumor cell or a second autologous tumor cell can be modified by introduction of a vector comprising a nucleic acid sequence encoding one or more tumor-associated antigens operatively linked to a promoter and expression/control sequences necessary for expression thereof. The nucleic acid sequence encoding the one or more tumor-associated antigens can be introduced into the same or a different autologous tumor cell using the same or a different vector. The nucleic acid sequence encoding the one or more tumor-associated antigens may or may not further comprise a selectable marker sequence operatively linked to a promoter. Desirably, the autologous tumor cell expresses high levels of GM-CSF and/or the one or more prostate tumor-associated antigens.

Allogeneic Cells

In one embodiment, genetically modified allogeneic cells containing a TLR4 agonist (e.g., comprising TLR agonists in association with liposomal vehicle) can enhance tumor immunogenicity. As used herein, a "neoplastic cell line" comprises cells that were initially derived from a tumor or other neoplastic cell. Such cells typically exhibit indefinite growth in culture. In one aspect, the method for enhancing an immune response from a subject involves: (a) obtaining a neoplastic cell line; (b) genetically modifying the cell line to render the cells capable of producing an increased level of a cytokine, e.g., GM-CSF; (c) contacting the cells of TLR agonists under conditions such that the cells take up the agonist; (d) rendering the modified neoplastic cell line proliferation incompetent; and (d) administering the neoplastic cell line to a subject having or having a propensity to develop a neoplasia of the same type as that from which the neoplastic cell line was obtained. In some embodiments, the administered cells are allogeneic and are or are not MHC-matched to the subject. Such allogeneic lines provide the advantage that they can be prepared in advance, characterized, aliquoted in vials containing a known amount of a TLR4 agonist and producing a comparable amount of a cytokine are stored (i.e. frozen) such that well characterized cells are available for administration to a subject. Methods for the production of genetically modified allogeneic cells are described for example in WO 00/72686, expressly incorporated by reference herein.

Any suitable route of administration can be used to introduce an allogeneic cell line composition into the patient, preferably, the composition is administered intradermally, subcutaneously or intratumorally.

TLR Agonists

Any suitable TLR agonist, or combination of agonists, can be used in preparing the immunogenic composition provided herein, including: R848, GLA, bacterial lipopeptide, bacterial lipoprotein, bacterial lipoteichoic acid, mycobacterial lipoglycan, yeast zymosan, porin, viral double stranded RNA, lipopolysaccharide, Lipid A, monophosphoryl lipid A (MPL®), AGPs, Flagellin, Viral single stranded RNA, imidazoquinolines, Bacterial DNA, CpG DNA, hemozoin, Uropathogenic bacteria, and protozoan profilin. These TLR agonists are known in the art and described, for example, by Reed et al., Trends in Immunol. 30:23-32, 2008, which further provides a review of adjuvants and vehicles. Reed supra is incorporated by reference herein in its entirety.

Administration

Neoplastic cells that have been genetically modified to express a cytokine (e.g., GM-CSF) and that comprise TLR agonists may be cryopreserved prior to administration. Preferably, such cells are treated to render them unable to proliferate ("proliferation-incompetent"). Most preferably, such cells are rendered proliferation-incompetent by irradiation which allows proliferation incompetence, but still allows the production of GM-CSF prior to ultimate cell death. In one embodiment, a cell of the invention is irradiated at a dose of from about 50 to about 200 rads/minute or from about 120 to about 140 rads/min prior to administration to the patient. Preferably, the cells are irradiated with a total dose sufficient to inhibit substantially 100% of the cells from further proliferation. Desirably the cells are irradiated with a total dose of from about 10,000 to 20,000 rads, optimally, with about 15,000 rads.

Typically more than one administration of cytokine (e.g., GM-CSF)-expressing cells comprising TLR agonists is delivered to the subject in a course of treatment. Dependent upon the particular course of treatment, multiple injections may be given at a single time point with the treatment repeated at various time intervals. For example, an initial or "priming" treatment may be followed by one or more "booster" treatments. Such "priming" and "booster" treatments are typically delivered by the same route of administration and/or at about the same site. When multiple doses are administered, the first immunization dose may be higher than subsequent immunization doses. For example, a $5 \times 10^{7-8}$ primedose may be followed by several booster doses of $10^{7-8}$ to $3 \times 10^{7-9}$ GM-CSF and tumor antigen producing cells.

A single injection of genetically modified cells comprising TLR agonists is typically between at least about $10^5$ to $10^9$ cells, e.g., $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $5 \times 10^7$, $\times 10^8$, $\times 10^9$ cells. The number of cytokine and tumor antigen producing cells may be adjusted according, for example, to the level of cytokine and/or tumor antigen produced by a given cellular immunotherapy composition. In preferred embodiments the modified cells are injected either intramusculary or intravenously.

In some embodiments, cytokine-producing cells of the cellular immunotherapy are administered in a dose that is capable of producing at least 1, 5, 10, 25, 75, 100, 200, 300, 400, 500 ng of GM-CSF per 24 hours per one million cells. In some embodiments, an immunogenic composition of the invention is administered in a dose that is capable of producing at least 500 ng of a particular tumor antigen per 24 hours per one million cells. Determination of optimal cell dosage and ratios is a matter of routine determination and within the skill of a practitioner of ordinary skill, in light of the disclosure provided herein.

Cells of the invention are processed to remove most additional components used in preparing the cells. In particular, fetal calf serum, bovine serum components, or other biological supplements in the culture medium are removed. In one embodiment, the cells are washed, such as by repeated gentle centrifugation, into a suitable pharmacologically compatible excipient. Compatible excipients include various cell culture media, isotonic saline, with or without a physiologically compatible buffer, for example, phosphate or hepes, and nutrients such as dextrose, physiologically compatible ions, or amino acids, particularly those devoid of other immunogenic components. A composition for administration in vivo can comprise appropriate carriers or diluents, which further can be pharmaceutically acceptable. For example, carrying reagents, such as albumin and blood plasma fractions and inactive thickening agents, may be used. The means of making such a composition have been described in the art. See, e.g., Remington's Pharmaceutical Sciences 19th edition, Genarro, A. Ed. (1995).

In pharmaceutical dosage form, the immunogenic compositions described herein can be used alone or in appropriate association, as well as in combination, with other pharmaceutically active compounds as are known in the art.

Pharmaceutical Therapeutics

The invention includes neoplastic cell-based vaccines that are useful for the treatment of neoplasia (e.g., a proliferation-incompetent neoplastic cell expressing GM-CSF and comprising a TLR4 agonist or fragment thereof). In one particular embodiment, the immunogenic compositions of the invention are useful for inducing or enhancing an immune response against a neoplasia or a tumor specific antigen. The phrase "enhanced immune response" as used herein means that a detectable increase of a specific immune activation is detectable (e.g. an increase in B-cell and/or T-cell response). An example of an enhanced immune response is an increase in the amount of an antibody that binds an antigen which is detected a lower level prior to administration of a cytokine-expressing cellular vaccine of the invention. Another example, is an increased cellular immune response. A cellular immune response involves T cells, and can be observed in vitro (e.g. measured by a Chromium release assay) or in vivo. An enhanced immune response is typically accompanied by an increase of a specific population of immune cells In another embodiment, the immunogenic compositions of the invention are useful for inhibiting neoplastic cell growth. The phrase "inhibiting neoplastic growth" refers to any measurable decrease in tumor mass, tumor volume, amount of tumor cells or growth rate of the tumor. Measurable decreases in tumor mass can be detected by numerous methods known to those skilled in the art. These include direct measurement of accessible tumors, counting of tumor cells (e.g. present in blood), measurements of tumor antigens (e.g. Prostate Specific Antigen (PSA), Alphafetoprotein (AFP) and various visualization techniques (e.g. MRI, CAT-scan and X-rays). Decreases in the tumor growth rate typically correlates with longer survival time for a subject with cancer. In still other embodiments, cell-based vaccines of the invention are useful for preventing or reducing tumor growth and/or the propensity of a neoplastic cell to invade a surrounding tissue or to otherwise metastasize. For therapeutic uses, the vaccines disclosed herein may be administered systemically, for example, formulated in a pharmaceutically-acceptable buffer such as physiological saline, or locally. Preferable routes of administration include, for example, intertumoral, peritumoral, subcutaneous, intravenous, interperitoneally, intramuscular, or intradermal injections that are sufficient to induce or enhance an immune response. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia, although in certain instances lower amounts will be needed because of the increased specificity of the compound.

Formulation of Pharmaceutical Compositions

The administration of a cell-based vaccines for the treatment of neoplasia may be by any suitable means that results in a concentration of the vaccine that, combined with other components, is effective in ameliorating, reducing, or stabilizing a neoplasia. The vaccine may be contained in any appropriate amount in any suitable carrier substance, and is generally present in an amount of 1-95% by weight of the total weight of the composition. The cell-based vaccine may be provided in a dosage form that is suitable for parenteral (e.g., subcutaneously, intravenously, intramuscularly, or intraperitoneally) administration route. The preferred method of administration is either intramuscularly, intratumoral, or intravenous infusion. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Parenteral Compositions

The pharmaceutical composition comprising the cell-based vaccine may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Combination Therapies

Optionally, cancer vaccine based therapeutics of the invention may be administered in combination with any other chemotherapeutic; such methods are known to the skilled artisan and described in Remington's Pharmaceutical Sciences by E. W. Martin. In particular, an immunogenic composition of the invention can be administered in combination with any one or more of abiraterone acetate, altretamine, anhydrovinblastine, auristatin, bexarotene, bicalutamide, BMS184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly- I -Lproline-t-butylamide (SEQ ID NO: 1), cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine (BCNU),cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In the combination therapies of the invention, the therapy components are administered simultaneously, or within 1, 3, 5, 7, 14, 21 or 28 days of each other, in amounts sufficient to inhibit the growth of a neoplasm. Depending on the type of cancer and its stage of development, the combination therapy can be used to treat cancer, to slow the spreading of the cancer, to slow the cancer's growth, to kill or arrest cancer cells that may have spread to other parts of the body from the original tumor, to relieve symptoms caused by the cancer, or to prevent cancer in the first place. Combination therapy can also help people live more comfortably by eliminating cancer cells that cause pain or discomfort.

The administration of a combination of the present invention allows for the administration of lower doses of each compound, providing similar efficacy and lower toxicity compared to administration of either compound alone. Alternatively, such combinations result in improved efficacy in treating neoplasms with similar or reduced toxicity.

Kits

The invention provides kits for the treatment or prevention of neoplasia. In one embodiment, the kit includes a therapeutic or prophylactic composition containing an effective amount of a tumor cell-based vaccine in unit dosage form. In some embodiments, the kit comprises a sterile container which contains a therapeutic or prophylactic cellular composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired a tumor cell-based vaccine of the invention is provided together with instructions for administering the vaccine to a subject having or at risk of developing cancer (e.g., melanoma, breast cancer). The instructions will generally include information about the use of the composition for the treatment or prevention of neoplasia. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Formulation of TLR Agonist Enhanced GVAX (TEGVAX)

In order to enhance locoregional innate immune cell activation as well as minimize systemic toxicity of Toll like receptor 4 (TLR4) stimulation and minimize TLR4R stimulation on tumor cells, lipopolysacharide (LPS) was formulated into GVAX (TEGVAX—TLR4 enhanced GVAX). A commercially available liposome vector—Lipofectamine—was used to optimize absorption of LPS into GVAX cells prior to lethal irradiation. In order to quantitate the extent of absorption, LPS-DIPYrromethene BOron Difluoride (BO-DIPY) fluorophore was used to test various conditions for optimization to have 98% of the cells formulated with LPS-BODIPY (FIG. 1). In order to quantitate the total amount of LPS absorbed per cell, Limulus Amebocyte Lysate (LAL) assay (Cambrex) was used to demonstrate that 4.73+/−0.2 ng of LPS was absorbed into $5 \times 10^5$ cells with the lipofectamine method that optimized LPS formulation. For each of the in vivo murine tumor experiments, aliquots of TEGVAX were tested using LAL assay as well as GM-CSF ELISA assay to ensure comparable amount of LPS and GM-CSF in the TEGVAX formulation. The typical GM-CSF secreted ranged from 50-200 ng/ml/$10^6$ cells/day.

Example 2

TEGVAX Induces In Vivo Anti-tumor Response in Multiple Murine Cancer Models

Figure 7:
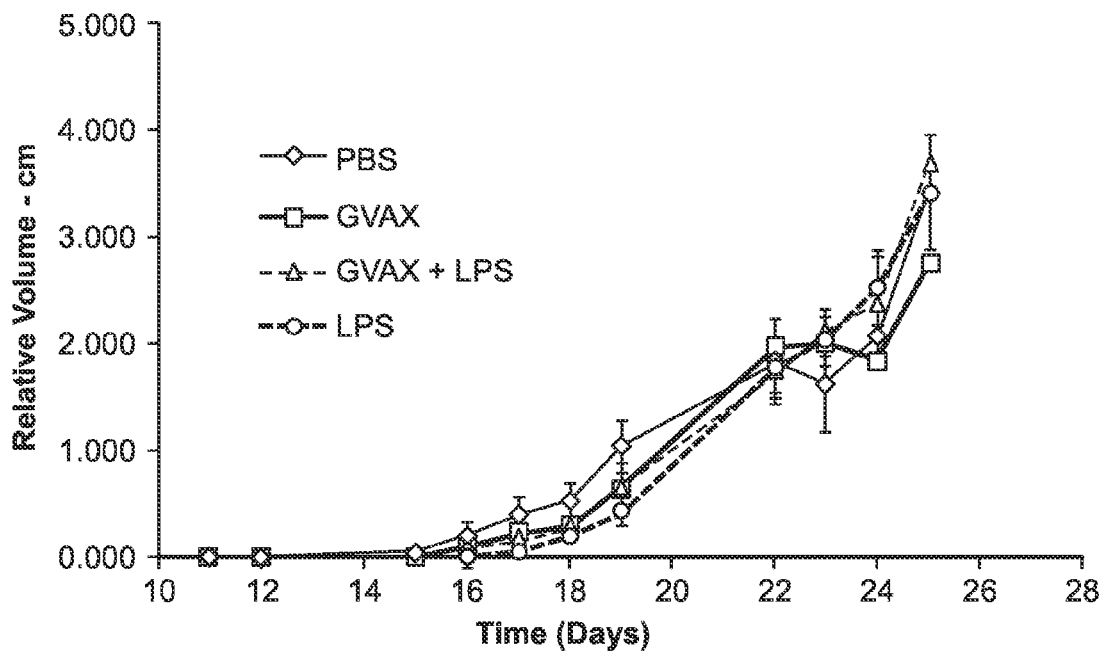
FIG. 7 shows that GVAX with equimolar LPS injected separately without formulation do not induce an anti -tumor response. B16 bearing mice were treated peritumorally with either GVAX, LPS, or with a mixture of LPS and GVAX without liposomal formulation. Equimolar amounts of LPS as used in FIG. 2 were injected peritumorally in these experiments.
Figure 8:
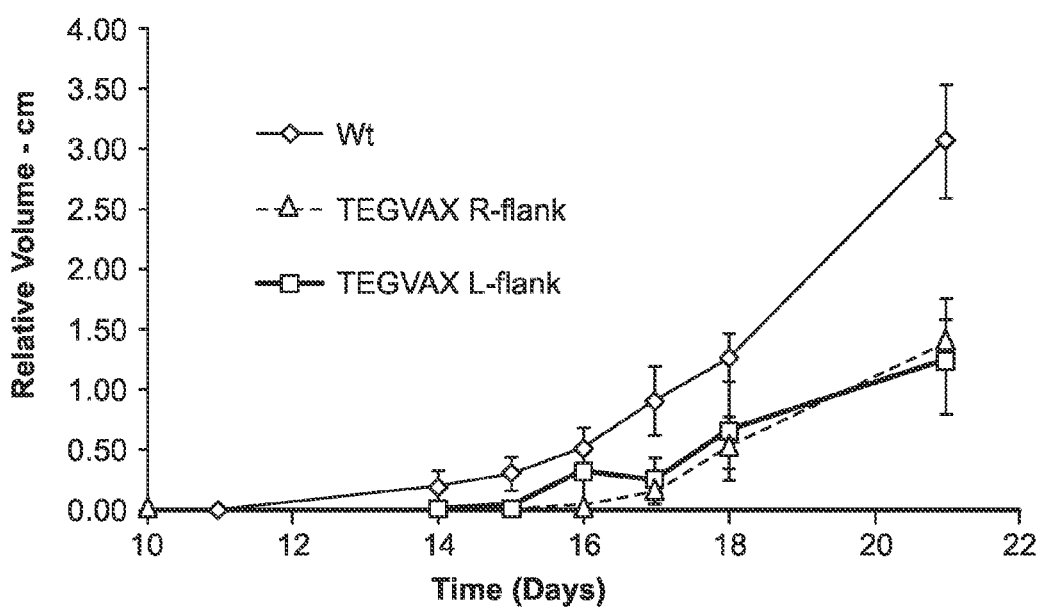
FIG. 8 shows that TEGVAX can also induce a systemic anti-tumor response. Using the B16 tumor model, mice were treated with either TEGVAX peritumorally or TEGVAX injected into the contralateral limb from the site of tumor inoculation. Both TEGVAX groups showed similar in vivo tumor growth rate.

The efficacy of TEGVAX was initially tested in a B16 melanoma murine model whereby TEGVAX was delivered intratumorally 3 to 5 days after tumor inoculation in a therapeutic model. Part of the rationale for intratumoral injection was to ensure that locoregional antigen presenting cells (APCs) that circulate between the tumor and the draining lymph nodes were targeted. These time-points were selected because anergic and tolerant tumor specific T-cells were present as early as 3 days after B16 injection. As shown in FIG. 2, TEGVAX decreased the growth rate of the B16 tumor in comparison to GVAX treatment. These statistically significant differences in growth rate translated to survival curve differences (FIG. 2). However, all the C57Bl/6 mice treated with TEGVAX eventually developed large tumors at the site of injection. Given that 4.73 ng of LPS per $5 \times 10^5$ GVAX cells was measured, control experiments were performed whereby an equimolar amount of LPS was injected peritumorally as in the TEGVAX treatment group. These mice had no differences in growth rate or survival as tumor-bearing mice treated with GVAX or PBS (FIG. 7). Equimolar LPS injected with GVAX without liposomal formulation also did not demonstrate an anti-tumor response in comparison to the PBS control group, suggesting that the intracellular formulation of LPS is important for its anti-tumor response (FIG. 7). TEGVAX also induced a systemic anti-tumor response (FIG. 8). Using the B16 melanoma model, mice were treated with TEGVAX either peritumorally or in the contralateral limb from the site of tumor inoculation, both treated groups showed similar in vivo tumor growth rate (FIG. 8).

To test if TEGVAX can also demonstrate an anti-tumor response in other murine tumor models, SCCFVII/SF cells were subcutaneously injected into the flanks of syngeneic C3H/HeOUJ mice with a wild-type TLR4R (FIG. 2). Once the tumor was palpable, the tumor was treated with either TEGVAX or GVAX prepared from murine SCCFVII/SF squamous cell carcinoma cells. Comparable to the TEGVAX experiments with B16 model, TEGVAX showed significant anti-tumor response. Once again, all the mice treated with TEGVAX eventually developed bulky tumors that required euthanasia. Orthotopic injection was not performed due to inaccuracies inherent in measuring tongue and floor of mouth tumor in SCCFVII/SF mice models.

Lastly, TEGVAX was also tested in CT26 colon carcinoma model, which also showed an anti-tumor response whereby the growth rate of the transplanted tumor was statistically slower than CT26 tumor treated with GVAX alone (FIG. 2). For CT26, 40-60% of the mice treated with TEGVAX actually had regression of tumor. CT26 cells were harvested from the mice that survived and the tumors were re-transplanted, and none grew out any tumor, demonstrating a complete immunotherapeutic cure. For the CT26 model, LPS formulated with lethally irradiated HEK 293 cells in equimolar amounts as TEGVAX was also tested. LPS formulated into cell based vaccine without an identical set of tumor antigens and GMCSF did not elicit an anti-tumor response in the CT26 model.

Example 3

Anti-tumor Response to TEGVAX is MyD88 Dependent

In order to verify that the in vivo anti-tumor effects noted above were in fact due to the introduction of TLR4 signaling, B16 tumor was inoculated into C57Bl/6 mice having MyD88−/−genotype. The tumor was then was treated with TEGVAX or GVAX. FIG. 3 shows that the enhanced anti-tumor response with the addition of TLR4 agonist formulated into GVAX cells are, in fact, secondary to TLR4 stimulation. A mild difference noted early in the GVAX group eventually overlapped with the growth curve of the PBS treated group (FIG. 7). MyD88 is an essential intracellular mediator of TLR4 signaling, and the absence of TLR4 signaling in MyD88 null mice no longer demonstrated the enhanced in vivo anti-tumor response noted consistently in wild type C57Bl/6 mice.

Example 4

Figure 4A:
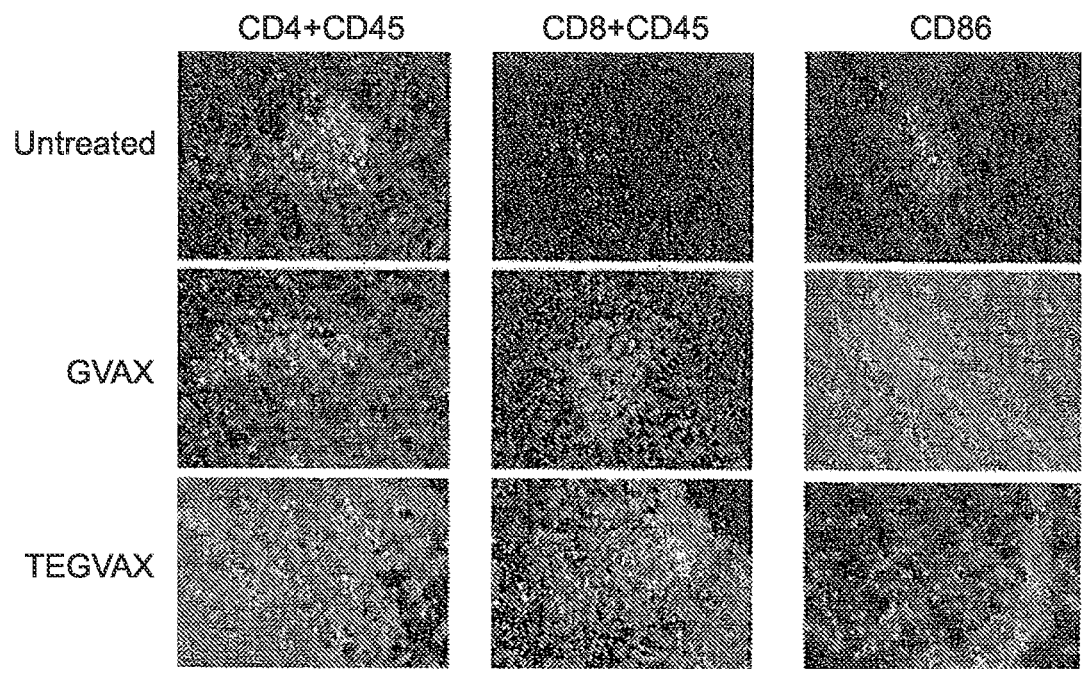
FIGS. 4A and 4B show that TEGVAX treatment increases the lymphocytic and antigen presenting cell infiltration into the tumor microenvironment.
Figure 4B:
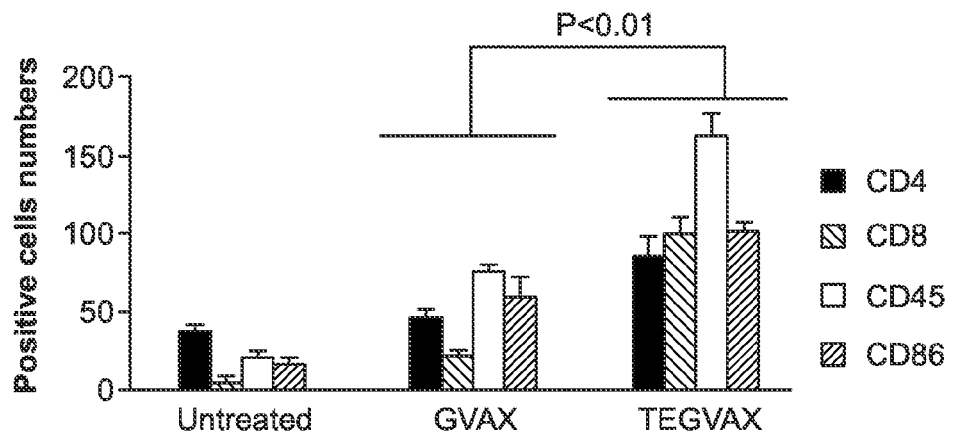

TEGVAX Induces Enhancement of T-cell Infiltration and APCs in the Tumor Microenvironment In order to examine the potential mechanism of the in vivo anti-tumor responses from TEGVAX treatment, the tumor tissue was harvested after treatments and analyzed for lymphocytic infiltrate. As shown in FIG. 4, tumor treated with TEGVAX had quantitatively increased CD4 and CD8 infiltration compared to the control treated and the GVAX treated tumors. Moreover, given the hypothesis that TLR4 agonist stimulates the locoregional professional APCs to mature, immunostaining was performed with antibodies against CD86 and a quantitative enhancement of CD86+ cells in the tumor microenvironment treated with TEGVAX was noted. Whether macrophages were increased in the tumor tissue was also examined, but no significant differences in the infiltration of F4+ macrophages between the treatment groups was found.

Example 5

Augmentation of Dendritic Cell Activation in the Locally Draining Lymph Nodes

The immunostaining data from FIG. 4 were consistent with the hypothesis that TLR4 agonist formulated cell vaccines can increase the number of activated locoregional dendritic cells. DCs are important primary antigen processing cells that can dictate whether effector cells become toleragenic or cytotoxic. Without wishing to be bound by theory, it is likely that LPS absorbed into GVAX is phagocytosed into the infiltrating DCs as cellular debris and micelles with tumor antigens.

Figure 5:
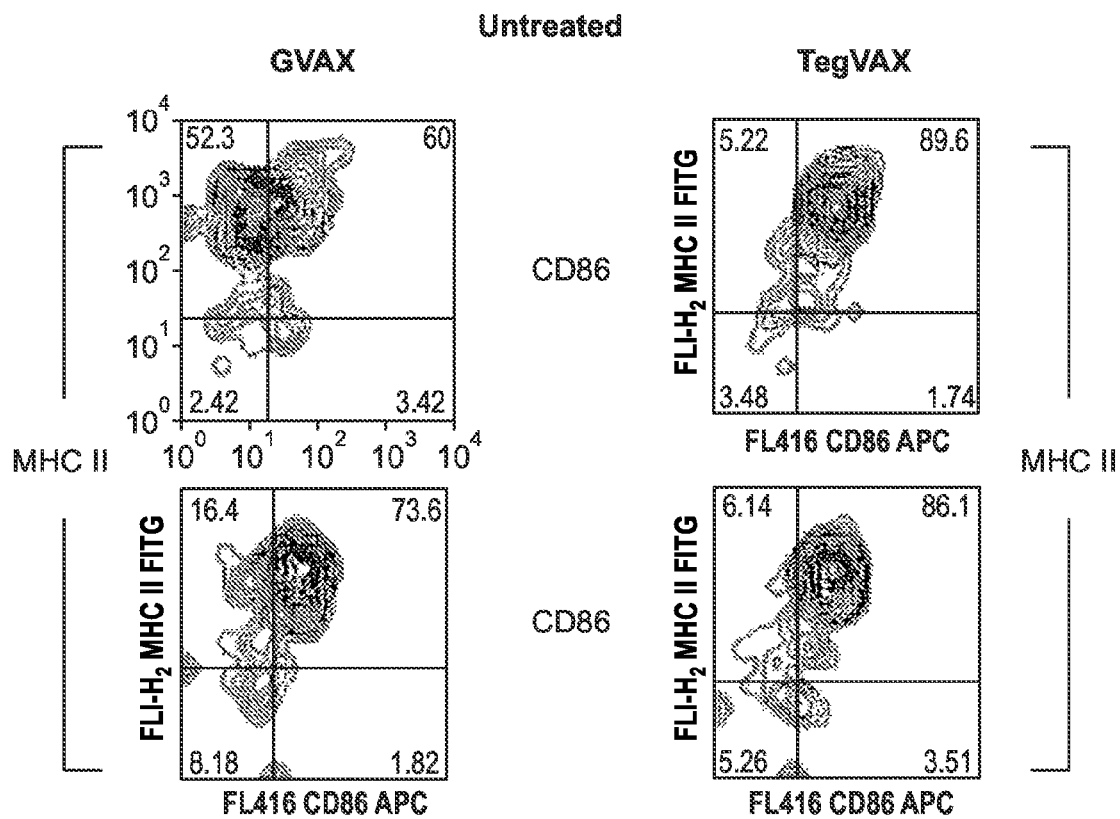
FIG. 5 shows that TEGVAX treatment increases activated dendritic cells (DC) in the draining lymph nodes (DLN). CT26 tumor bearing Balb/c mice were treated with PBS (not shown), GVAX, or TEGVAX peritumorally 3 days after the tumor injection. DCs were isolated from the DLN 5-7 days after treatment. B220+CD11c+ cells were gated and CD86, MHCCII, and CD80 staining were analyzed as shown. TEGVAX had increased number of CD86+MHCII+ as well as CD80+MHCII+ DCs in the DLN in comparison to GVAX treated group.

Thus, it seemed likely that there would be increased number of activated locoregional DC population with TEGVAX treatment. In order to test this hypothesis, dendritic cells were purified from the draining lymph nodes from tumor bearing mice treated with either PBS, GVAX, or TEGVAX and gated for the conventional DC population with B220 and CD11c. Multiparametric staining of DC activation marker CD86, CD80, and MHCII from these gated cells shows that dendritic cells from the TEGVAX treated group has greater population of activated DCs (FIG. 5) in comparison to the GVAX treated group or the control treated group.

Example 6

Tumor Specific Cytotoxic T-cells are Expanded in Mice Treated with TEGVAX

Figure 6A:
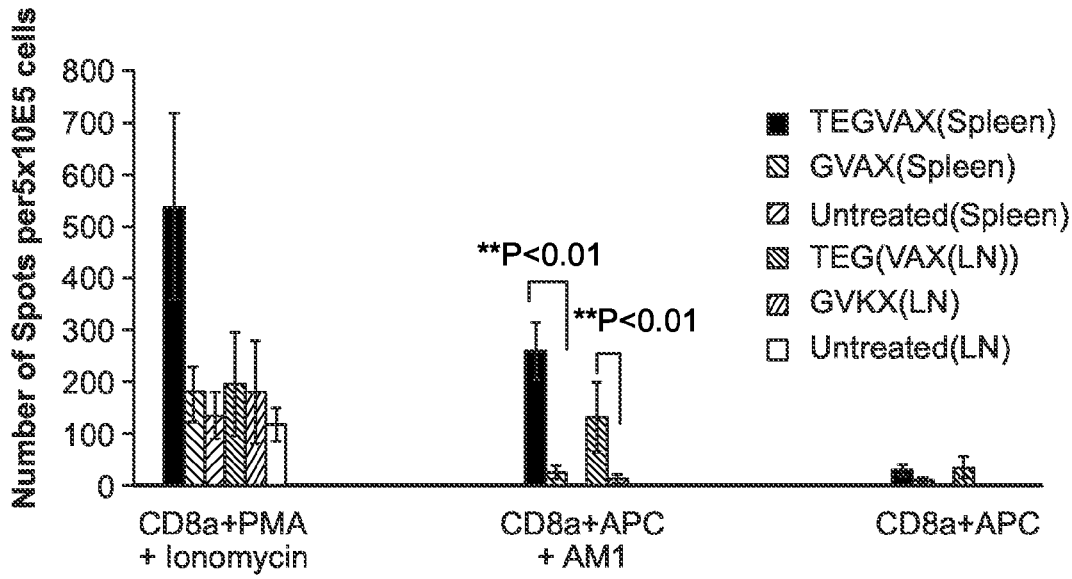
FIGS. 6A and 6B show that TEGVAX treatment increases the number of tumor specific CD8+ T-cells. CT26 bearing Balb/c mice were treated with PBS, GVAX, or TEGVAX peritumorally 3 days, and 5 days later CD8+ cells were isolated and purified from the spleen and lymph nodes. ELISPOT assays were performed using 4T1 cells as APCs and AH1 peptide, and IFN-levels were measured.
Figure 6B:
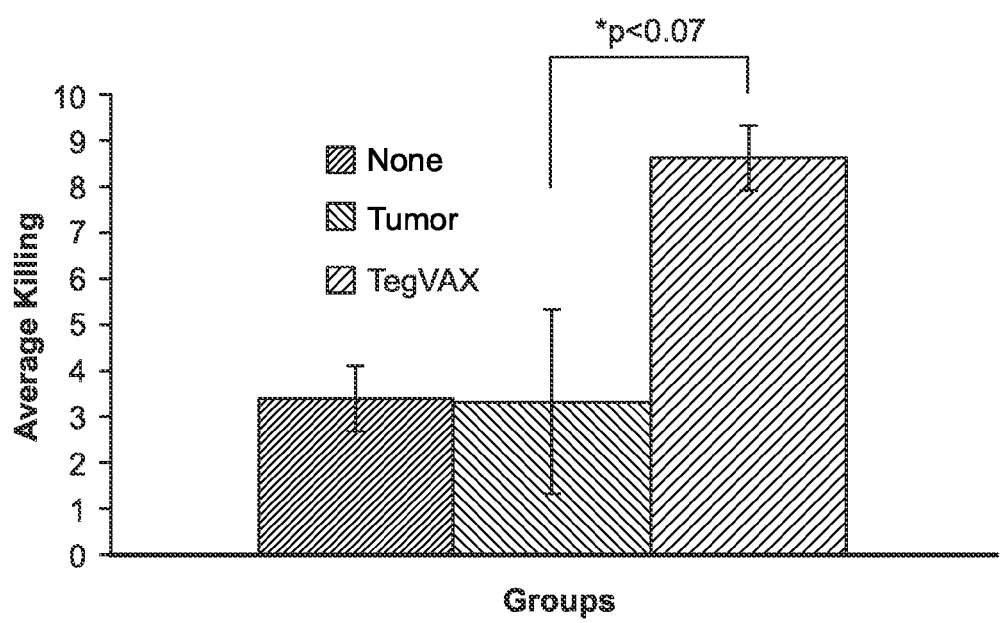

One rationale for studying the CT26 model in conjunction with SCCFVII/SF and B16 model was the availability of reagents for quantitation of AH1-specific cytotoxic T-cells. To test if the in vivo anti-tumor responses for TEGVAX that activates locoregional dendritic cells can increase the downstream population of tumor specific cytotoxic effector cells, ELISPOT assays were performed. Using the immunogenic MHC class I $L^d$ restricted AH1 peptides, T-cells from the draining lymph node and spleen were harvested and IFN-producing cytotoxic T-cells screened in the presence of AH1 peptides (the immunodominant peptide for CT26 cells pulsed with APC in the ELISPOT assay. While minimal AH1 specific T-cells were detected on day 5 after treatment with TEGVAX, by day 8, there were statistically significant AH1 specific T-cells in the TEGVAX group in both the draining lymph nodes and the spleen as shown in FIG. 6A. In vivo cytotoxic T-lymphocyte (CTL) assays also demonstrated enhanced cytotoxic T-cell priming for the AH1 peptide in the TEGVAX treated group in comparison to the untreated group (FIG. 6B). In vivo CTL assays with p15E specific T-cell from the B16 model also demonstrated enhanced p15E-specific T-cells in the TEGVAX group.

Example 7

TLR4 Agonist in Combination with GVAX Reduced Tumor Cell Growth and Increased the Number of AH1-Specific Cytotoxic T-cells As reported above, TEGVAX improved in vivo tumor responses in three separate murine models. In the B16 melanoma model, the CT26 colon carcinoma models, as well as the SCCVII tongue squamous model, TEGVAX injected intratumorally into established tumors reduced tumor growth in comparison to GVAX alone. Systemic treatment using TEGVAX after tumor inoculation also reduced B16 growth rate in vivo. In order to examine the immunological mechanism inducing the anti-tumor responses, the CT26 murine model was used to study the anti-tumor cytotoxic T-cell (CTL) responses. Using the well characterized Elispot assay and in vivo CTL assay, TEGVAX treated mice showed increased number of AH1-specific cytotoxic T-cells (CTL) by day 8 after treatment. In these experiments, the rate of tumor growth rate in the preclinical models was reduced by combining TLR4 agonist with GVAX.

Example 8

Figure 9:
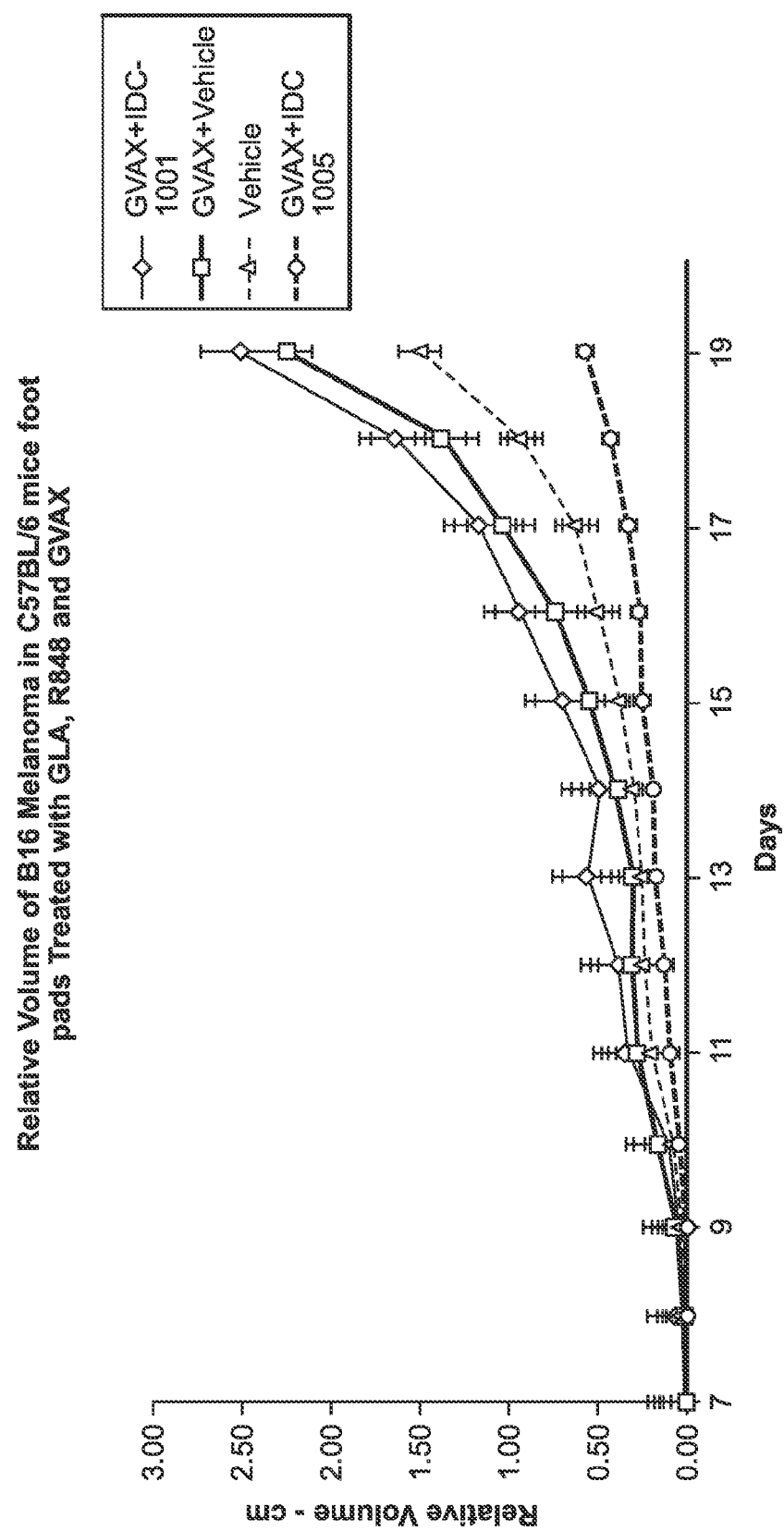
FIG. 9 is a graph showing that the combination of GVAX, R848, and GLA prevented melanoma tumor cell growth. GVAX and its formulations with various TLR agonists were injected 3 days after B16 tumor inoculation. The tumor was not palpable at the time of vaccine treatments. The relative growth rate of the tumor was followed for each group. For the B16 tumor treated with GVAX, GLA, and R848, the tumor growth was initially noted to be less than the other groups, and in some of these mice, these tumor regressed.

A Synthetic TLR4 Agonist—Glycopyranosyl Lipid A Analogue (GLA)—in Combination with GVAX and a TLR7 and TLR8 Agonist (R848) Significantly Reduced the Growth of Melanoma Cells To determine whether more than one type of TLR signaling in the tumor microenvironment can improve upon the anti-tumor response another form of TLR4 agonist, GLA, a synthetic glycopyranosyl lipid A analogue, was used with the GVAX. GLA formulated GVAX was also combined with R848, a TLR7 and TLR8 agonist. In vivo tumor treatment experiments were performed with B16 melanoma mice. Using the B16 melanoma model, the combination of GVAX, GLA, and R848 prevented the growth of the aggressive B16 tumor in wildtype mice (FIG. 9).

The vaccine formulations were injected 2-4 days after tumor inoculation. Typically, GVAX by itself does not prevent the growth of the B16 in vivo in these poorly immunogenic tumor cells. When these mice were re-injected with B16 melanoma cell lines, the challenge tumor cells did not grow. Both ELISPOT and in vivo CTL assays were performed to quantitate p15E specific CD8+ T-cells, and the mice treated with GVAX, GLA, R848 had significantly more p15E specific CD8+ T-cells than mice treated with GVAX alone.

Example 9

A Combination of GVAX/GLA/R848 Enhanced Dendritic Cell Activation

Figure 10:
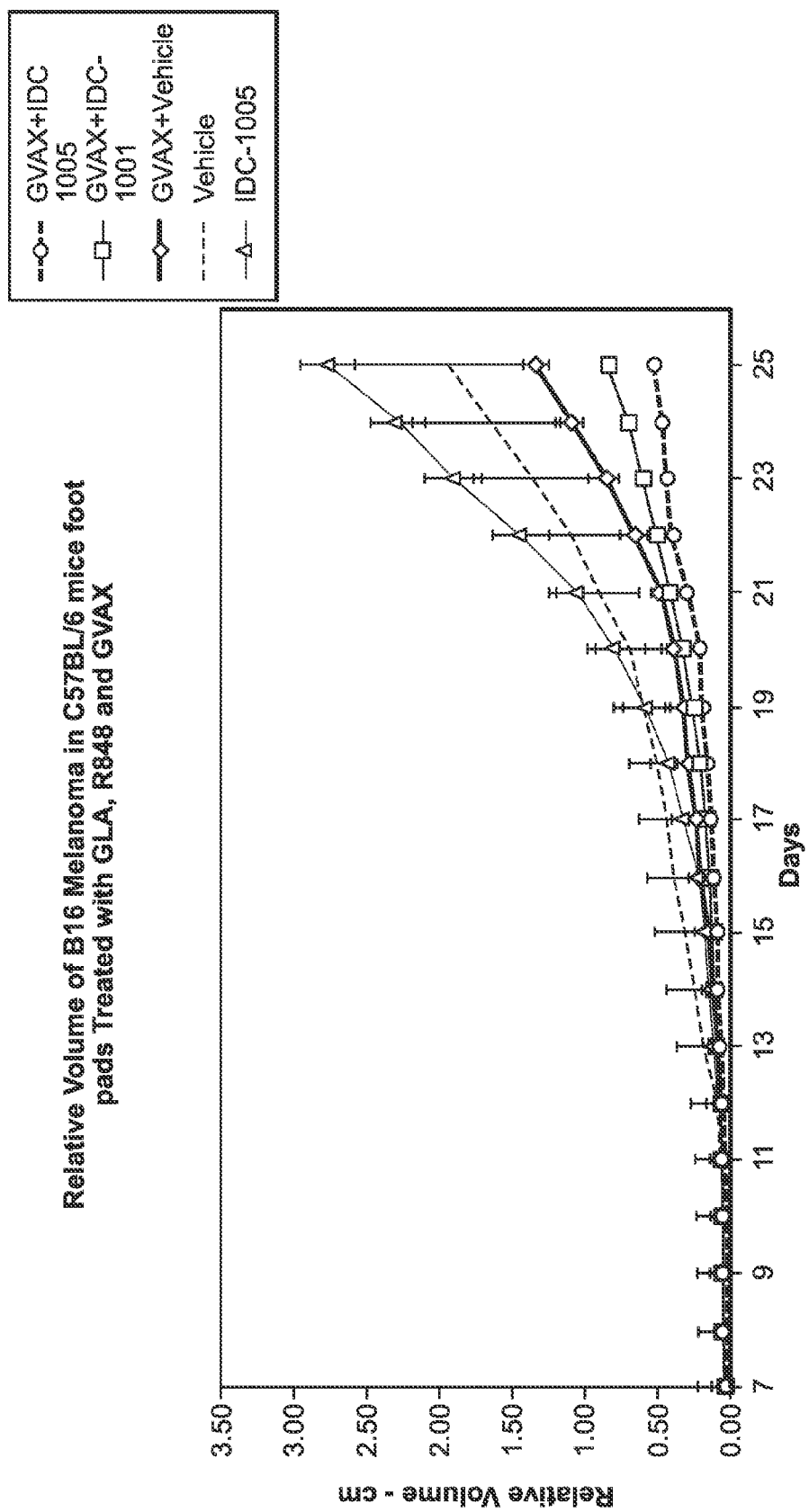
FIG. 10 is a graph showing that TLR agonist enhanced GVAX reduced the tumor growth rate on established B16 tumor. B16 tumor cell was injected into the footpad, and once the tumor was palpable, the mice were treated with the vaccine formulations as note in the figure. The vaccines were injected into the contralateral limb.

In order to treat an organized tumor tissue, the GVAX/GLA/R848 formulation was used to treat palpable B16 tumor. The vaccine formulation was injected 7-10 days after tumor inoculation as site distant from the palpable tumor tissue. Once again the TLR agonist enhanced GVAX reduced the tumor growth rate (FIG. 10).

Figure 11B:
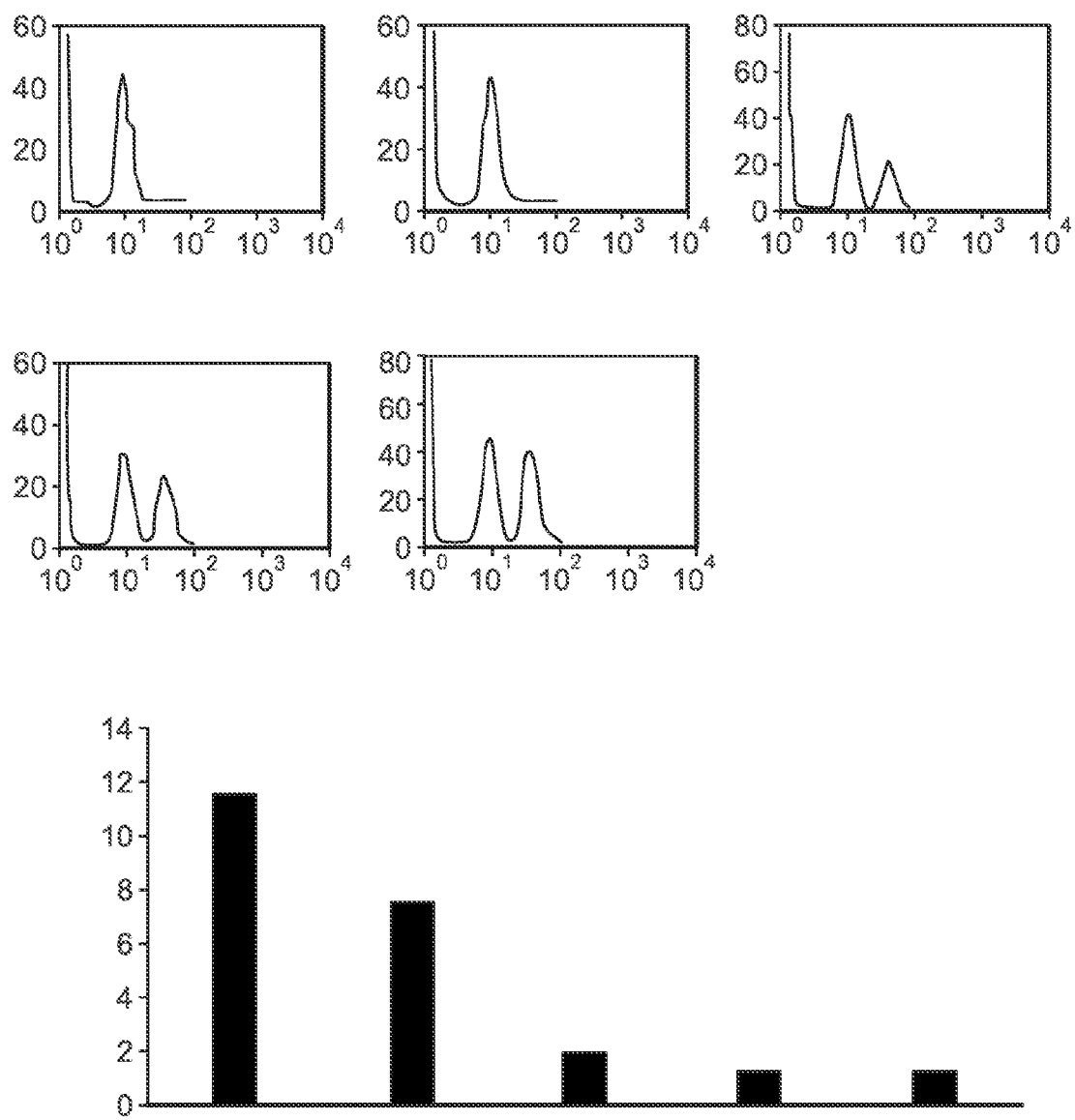

ELISPOT and in vivo CTL assays were performed in each of the groups to quantitate the level of p15E specific CTL, and the results demonstrated that the mice treated with GVAX/GLA/R848 had the highest number of p15E-specific T-cells that correlated with the in vivo tumor growth rate (FIG. 11A and FIG. 11B).

Figure 12:
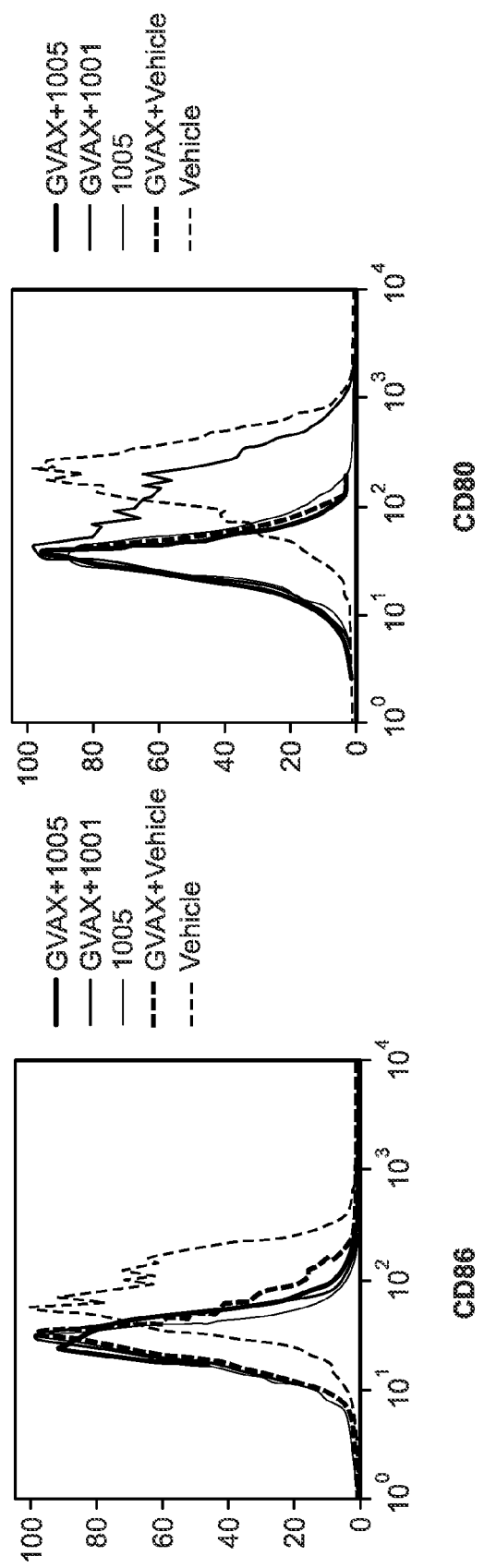
FIG. 12 provides two panels showing that mice treated with GVAX/GLA/R848 had significantly enhanced activated dendritic cells.

Given these anti-tumor responses with the GVAX/GLA/R848 formulation, it was hypothesized that the TLR agonist enhanced vaccines were stimulating the dendritic cells. Therefore, draining lymph nodes and the spleen from each treatment group was harvested, and the activation status of the dendritic cells was examined. Using CD80 and CD86 activation markers on CD11c+ and B220+ cells, the GVAX/GLA/R848 treated group showed significantly enhanced activated dendritic cells (FIG. 12).

The tumor tissue from each treatment group was analysed using immunohistochemistry. A higher number of CD4+, CD8+, and CD86+ cells was found in tumors treated with GVAX/GLA/R848. Lastly, the cytokine milieu was examined in each of the treatment groups to determine whether IL-12 was elevated in the mice treated with the TLR agonists. CD11c positive cells were harvested in both draining lymph nodes and the spleen, and the level of IL-12 cytokines was examined for the ability to direct the T-cell repertoire towards an anti-tumor Th1 response (FIG. 13A and FIG. 13B). GVAX/GLA/R848 treated mice had statistically significant number of CD11c+cells that express IL-12, which is the primary cytokine that directs the T-cell milieu towards a Th1 response. This was noted in both the draining lymph nodes and the spleen.

In summary, these results showed that a combinatorial approach using GVAX platform with multiple TLR agonists had increased efficacy in the treatment of solid tumors. A combination of GVAX with TLR4 and TLR7/8 agonists improves the anti-tumor response in vivo. The improved anti-tumor response is correlated with increased number of activated dendritic cells, increased number of tumor specific CTLs, and increased number of CD11c+ that can secrete I1-12 in the draining lymph nodes and the spleen.

Example 10

Figure 14:
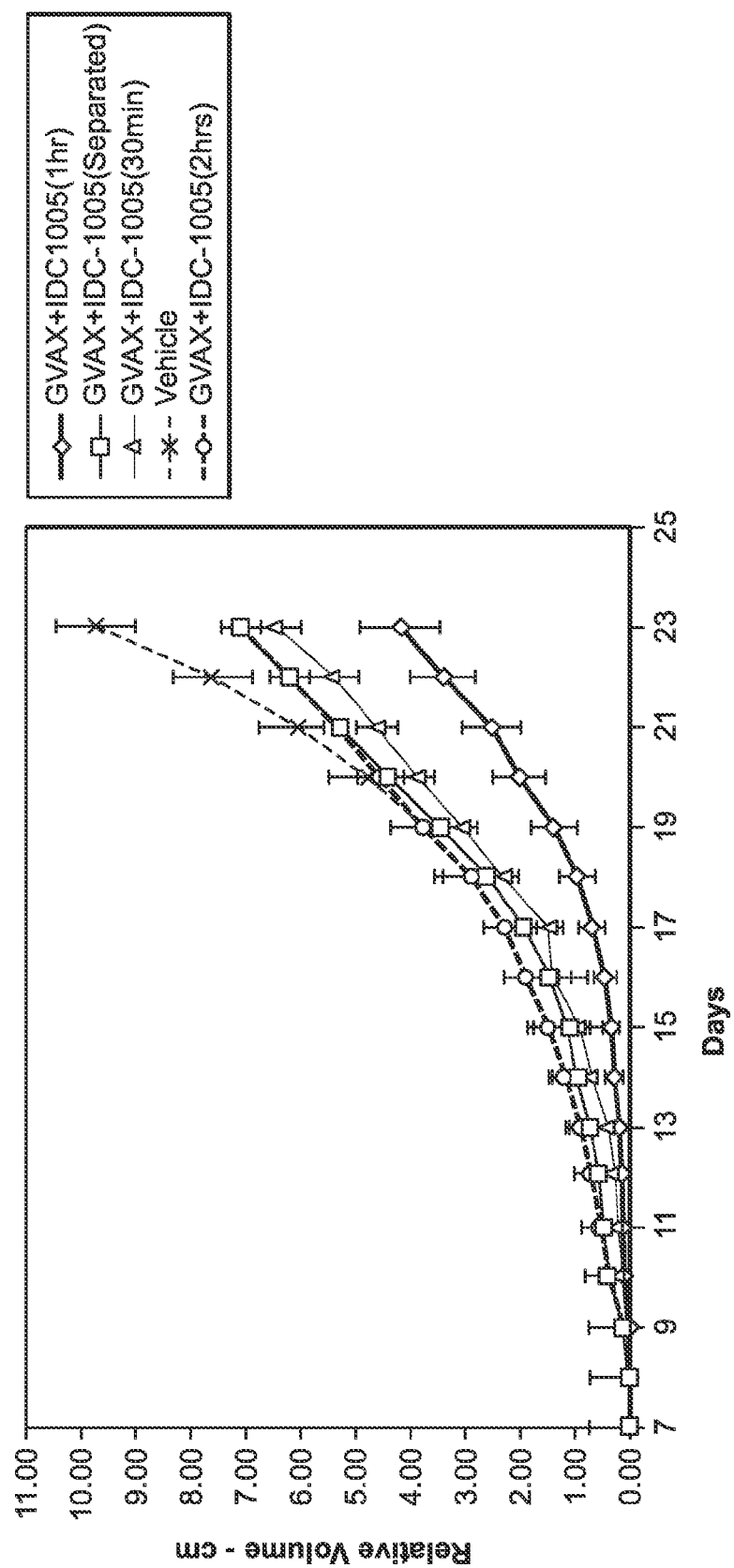
FIG. 14 is a graph showing the effects of various formulations of GVAX/GLA/R848 on established B16 tumors. IDC-1005 is GLA/R848 in the presence of vehicle comprising stable squalene oil-in water emulsion that contains phosphatidylcholine.

Specific Formulation Times of TLR Agonists with GVAX Cellular Vaccine Improves the In Vivo Efficacy of Anti-Tumor Activity The effects of the time of incubation of the TLR agonists with GVAX during the formation of the TEGVAX formulation on anti-tumor activity were evaluated. A panel of three TEGVAX formulations containing GLA/R848 and GVAX were prepared such that the length of incubation of the GLA/R848 with GVAX varied in each formulation (30 minutes, 1 hour, and 2 hours). Each of the TEGVAX formulations were administered to mice bearing established B16 tumors and the relative volume of the B16 tumors were measured over 24 days (FIG. 14). As a control GVAX and GLA/R848 were administered without mixing ("separated" in FIG. 14). An additional control consisted of vehicle alone. When GLA and R848 in the presence of vehicle were admixed with GVAX less than 30 minutes prior to irradiation, the formulation had no anti-tumor activity. The anti-tumor activity was also diminished when GVAX and TLR agonists were incubated for more than 2 hours. Maximal anti-tumor activity was seen in TEGVAX formulations when the GLA and R848 in the presence of vehicle were mixed with GVAX for one hour (FIG. 14).

The results described above were obtained using the following methods and materials.

Murine Tumor Cell Lines

The SCCFVII/SF head and neck squamous cell carcinoma, B16-F0 melanoma and B16-F0 transduced to secrete GM-CSF cell lines were cultured in RPMI 1640 media containing 10% heat-inactivated fetal calf serum, penicillin (100 U/ml) and streptomycin (100 U/ml). CT26 colorectal carcinoma cell line was cultured similarly with the addition of MEM nonessential amino acids (Sigma, St. Louis), 1 mM sodium pyruvate, and 2 mM of L-glutamine. The bystander B78HI cells transduced with GM-CSF were cultured in the same media has CT26 but with the addition of Hygromycin B from Streptomyces hygroscopicus (1 g/L) (Roche Applied Science, Indianapolis, Ind.). All cells were incubated at 37° C. in 5% humidified CO2. The GVAX vaccine cell lines tested in vaccination models whereby the vaccines were injected 10 days prior to tumor inoculation showed no tumor growth for all three GVAX lines.

Mice

Adult (>50 days of age) female C57BL/6, Balb/C, and C3H/HeOUJ mice were purchased from Jackson Laboratory and housed according to the Johns Hopkins Animal Care and Use Committee. C57BL/6 MyD88−/−mice were obtained from Dr. Franck Housseau (Johns Hopkins University).

TEGVAX Formulation

LipofectAMINE Reagent (120 µg/ml) and LPS from *Escherichia coli* 026:B6 (10-25 µg/ml) were combined into liposome complex. Cells for lipopolysaccharide (LPS) formulation were seeded at a density of $5 \times 10^5$ cells and after 24 hrs they were incubated with the liposome-LPS complex for 6 hrs, washed 5 times with PBS, and then injected into mice. To quantitate LPS incorporated into cells *Limulus Amebocyte* Lysate (LAL) assay (Cambrex) was performed as directed by the manufacturer. LPS (23 EU/ng) from 0 to 3.0 EU/ml were used as standards. Prior to lethal irradiation, the TEGVAX was cultured to ensure viable cell growth. Annexin staining verified no evidence of apoptosis after formulation.

For the GLA/R848 containing TEGVAX formulation, the vehicle for adsorbing the TLR agonists with the GVAX cells was a stable squalene oil-in water emulsion with phosphatidylcholine. The TLR agonists were prepared in the vehicle at a concentration of 1 mg/ml GLA and 0.2 mg/ml R848. Cultured GVAX cells were trypsinized and washed. After washing the cells were lethally irradiated with 10,000 RAD. GLA and R848 in the presence of vehicle were mixed with the irradiated GVAX cells and incubated at room temperature for 1 hour prior to injection into mice. Typically, 20 µl of GVAX cells and 20 µl of GLA/R848/vehicle were mixed prior to injection.

In Vivo Vaccine Treatment Assay

C57BL/6 mice were injected subcutaneously in the right flank with $5 \times 10^4$ B16-F0 cells. Three to five days post inoculation $10^6$ lethally irradiated (150 Gy) B16 GM-CSF (GVAX),$10^6$ lethally irradiated (150 Gy) LPS formulated GVAX (TEGVAX formulation) or LPS absorbed 293 cells were injected peritumorally. In some cases, the vaccines were injected in the contralateral limb from the tumor-inoculated limb. C3H/HeOUJ mice and Balb/c mice were used with SCCFVII/SF cells and CT26 cells, respectively with comparable methods.

Immunohistochemistry

Frozen CT26 tumor from mice was cut in 10 µm thickness and blocked with 1% BSA 30 minutes at room temperature. Anti-mouse CD45 (eBioscience) and anti-mouse CD4-Fluorescein isothiocyanate (FITC), CD8-FITC, CD86-FITC antibodies (BD Pharmingen) incubated at 4° C. for 1 hour were used as primary antibodies. Anti-CD45-Cy3 (Invitrogen) was used as secondary in some case. DAPI was used as counterstain for 10 minutes. Cells in 10 randomly selected fields at 40× magnification were counted. Nikon Eclipse F800 was the microscope, Nikon DS-Qi1mc was the camera, and NIS-Element AR 3.0 was the software used for this experiments. Spleens and draining lymph nodes from tumor challenged BL/6 mice was harvested five days post GVAX and TEGVAX treatment. Sliced spleens were enzymatically digested in media containing DNAse I (Roche)) and a commercially available blend of enzymes for tissue dissociation (LIBERASE BLENDZYME 2) (20,000 Mandl U/ml) (Roche). DC-enriched populations were obtained by depleting CD3+ and CD19+, and stained for CD11c+ and B220+. CD11c+ B220+ gated DC's were evaluated by multicolored FACS analysis using CD80, CD86, and MHCII antibodies from BD Biosciences.

ELISPOT Assay

Enzyme-linked immunosorbent spot (ELISPOT) plates (MultiScreen$_{HTS}$ filter plate, Millipore) were coated with a mouse interferon (IFN)-γ antibody (Ab) (MabTech) for 24 hours and 4T1 breast cancer cells were pulsed with 10 µg/ml of AH1 peptide overnight. The following day, spleens and lymph nodes were harvested from mice. $10^6$ CD8a+ cells were plated in triplicates to be co-cultured with $10^5$ unpulsed 4T1 cells, co-cultured with $10^5$ pulsed 4T1 cells, or stimulated with 1 µM of PMA and 10 ng/ml of ionomycin for a positive control. On the third day, the plate was incubated with a biotinylated anti-mouse IFN-γ Ab (MabTech) followed by incubation with Streptavidin-HRP for ELISPOT (BD). The plate was developed using AEC Substrate Reagent Set for ELISPOT (BD) and analyzing using an ELISPOT Plate Reader (Immunospot).

In Vivo CTL Assay

A commercially available reagent for in vivo tracing Cell-Trace™ CFSE Cell Proliferation Kit (Molecular Probes) was used to test the percent killing of CTLs in CT26 tumor challenged mice treated with or without TEGVAX. Splenocytes were processed and pulsed with either β-galactosidase (β-gal) or AH1 peptide at a concentration of 10 μg/ml for 90 minutes. The β-gal population was CFSE labeled low (0.5 μM) and the AH1 population was carboxyfluorescein diacetate succinimidyl ester (CFSE) labeled (5 μM). After a 10 minute incubation, both CFSE labeled cells were injected $10^7$ cells/mouse into the three groups of mice. Twenty-four hours post-injection, splenic cells were harvested and analyzed.

Statistical Analysis

Paired t-test was used to calculate two-tailed p value to estimate statistical significance of difference between two treatment groups. Statistically significant p values were labeled as follow: **$p<0.01$ and *$p<0.05$. Data were analyzed using Excel software.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An immunogenic composition comprising one or more proliferation-incompetent genetically modified neoplastic cells expressing a recombinant immune stimulatory cytokine, wherein the cytokine comprises granulocyte-macrophage colony-stimulating factor (GM-CSF), and wherein said neoplastic cells comprise at least one Toll-like receptor (TLR) agonist.

2. The immunogenic composition of claim 1, wherein the cell comprises comparable amounts of at least one TLR agonist and GM-CSF.

3. The immunogenic composition of claim 1, wherein the TLR agonist is a TLR4, TLR5, TLR6, TLR7 or TLR8, TLR9 agonist.

4. The immunogenic composition of claim 1, wherein the composition comprises a TLR4 agonist and a TLR7/8 agonist.

5. The immunogenic composition of claim 4, wherein the TLR4 agonist is lipopolysaccharide (LPS), an LPS fragment, or a synthetic glycopyranosyl lipid A analogue and the TLR7/8 analog is R848.

6. The immunogenic composition of claim 1, wherein the cells are rendered proliferation incompetent by irradiation.

7. The immunogenic composition of claim 1, wherein the one or more proliferation-incompetent genetically modified neoplastic cells is selected from the group consisting of leukemia, chronic myeloid leukemia, prostate cancer, head and neck cancer, Squamous Cell Carcinoma, tongue cancer, larynx cancer, tonsil cancer, hypopharynx cancer, nasalpharynx cancer, breast cancer, colon cancer, lung cancer, melanoma, pancreatic cancer, glioblastoma and brain cancer.

8. The immunogenic composition of claim 1, wherein the composition comprises at least about 1 ng of TLR4 agonist per $1 \times 10^5$ cells -10 ng of TLR4 agonist per $1 \times 10^5$ cells.

9. The immunogenic composition of claim 1, wherein the composition comprises at least about 3-5 ng of TLR agonist per $5 \times 10^5$ cells.

10. The immunogenic composition of claim 1, wherein the one or more proliferation-incompetent genetically modified neoplastic cells comprises a TLR agonist in association with Lipofectamine or other liposomal vectors.

11. The immunogenic composition of claim 10, wherein the one or more proliferation-incompetent genetically modified neoplastic cells comprises LPS/liposomal micelles.

12. The immunogenic composition of claim 1, further comprising cells that express one or more tumor antigens.

13. The immunogenic composition of claim 1, wherein the cells are autologous or allogeneic.

14. A vaccine for ameliorating a neoplasia in a subject, the vaccine comprising an effective amount of one or more proliferation-incompetent neoplastic cells expressing a recombinant immune stimulatory cytokine, wherein the cytokine comprises GM-CSF, and wherein said neoplastic cells comprise an effective amount of an exogenous Toll-like receptor (TLR) agonist in a pharmaceutically acceptable excipient.

15. The vaccine of claim 14, wherein the vaccine comprises a TLR4 agonist and a TLR7/8 agonist.

16. The immunogenic composition of claim 13, wherein the one or more proliferation-incompetent genetically modified neoplastic cells is derived from a cancer cell line or is derived from a tumor.

17. The immunogenic composition of claim 16, wherein the cancer cell line or tumor is selected from the group consisting of leukemia, chronic myeloid leukemia, prostate cancer, head and neck cancer, Squamous Cell Carcinoma, tongue cancer, larynx cancer, tonsil cancer, hypopharynx cancer, nasalpharynx cancer, breast cancer, colon cancer, lung cancer, melanoma, pancreatic cancer, glioblastoma and brain cancer.

18. A proliferation-incompetent neoplastic cell comprising an expression vector encoding GM-CSF and at least one TLR agonist.

19. A pharmaceutical composition for the treatment of neoplasia comprising an effective amount of the immunogenic composition of claim 1 and a pharmaceutically acceptable excipient.

20. A kit for the treatment of a neoplasia, the kit comprising an effective amount of the immunogenic composition of claim 1, and directions for using the kit.

* * * * *